US010786306B2

(12) United States Patent
Coates et al.

(10) Patent No.: US 10,786,306 B2
(45) Date of Patent: Sep. 29, 2020

(54) DENERVATION THERAPY

(71) Applicant: Medtronic Ardian Luxembourg S.a.r.l., Luxembourg (LU)

(72) Inventors: Paul J. Coates, Corte Madera, CA (US); Douglas A. Hettrick, Andover, MN (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 165 days.

(21) Appl. No.: 15/965,675

(22) Filed: Apr. 27, 2018

(65) Prior Publication Data

US 2019/0223955 A1 Jul. 25, 2019

Related U.S. Application Data

(60) Provisional application No. 62/621,351, filed on Jan. 24, 2018.

(51) Int. Cl.
*A61B 34/10* (2016.01)
*A61B 5/053* (2006.01)
(Continued)

(52) U.S. Cl.
CPC ............ *A61B 34/10* (2016.02); *A61B 5/0066* (2013.01); *A61B 5/055* (2013.01); *A61B 5/0536* (2013.01);
(Continued)

(58) Field of Classification Search
CPC ...... A61B 2090/3954; A61B 2090/378; A61B 2090/3762; A61B 2090/374;
(Continued)

(56) References Cited

U.S. PATENT DOCUMENTS 7,653,438 B2 1/2010 Deem et al.
8,347,891 B2 1/2013 Demarais et al.
(Continued)

FOREIGN PATENT DOCUMENTS

EP 2457615 12/2014
EP 2934357 11/2017
(Continued)

OTHER PUBLICATIONS

International Searching Authority, International Search Report and Written Opinion for International Application No. PCT/US2019/013630, dated Apr. 25, 2019, 16 pages.
(Continued)

*Primary Examiner* — Catherine M Voorhees

(57) ABSTRACT

Example systems and techniques for denervation, for example, renal denervation. In some examples, a processor determines one or more tissue characteristics of tissue proximate a target nerve and a blood vessel. The processor may generate, based on the one or more tissue characteristics, an estimated volume of influence of denervation therapy delivered by a therapy delivery device disposed within the blood vessel. The processor may generate a graphical user interface including a graphical representation of the tissue proximate the target nerve and the blood vessel and a graphical representation of the estimated volume of influence.

20 Claims, 14 Drawing Sheets

(51) Int. Cl.

| | |
|---|---|
| *A61B 5/00* | (2006.01) |
| *A61B 6/00* | (2006.01) |
| *A61B 6/03* | (2006.01) |
| *A61B 18/14* | (2006.01) |
| *A61B 18/06* | (2006.01) |
| *A61B 18/24* | (2006.01) |
| *A61B 34/00* | (2016.01) |
| *A61B 90/00* | (2016.01) |
| *A61B 5/055* | (2006.01) |
| *A61B 8/08* | (2006.01) |
| *A61B 5/20* | (2006.01) |
| *G16H 50/50* | (2018.01) |
| *A61B 17/32* | (2006.01) |
| *A61B 18/02* | (2006.01) |
| *A61B 18/18* | (2006.01) |
| *A61B 18/00* | (2006.01) |
| *A61B 6/12* | (2006.01) |
| *A61B 34/20* | (2016.01) |
| *A61B 8/00* | (2006.01) |

(52) U.S. Cl.
CPC ............ *A61B 5/201* (2013.01); *A61B 5/40* (2013.01); *A61B 5/407* (2013.01); *A61B 5/4041* (2013.01); *A61B 5/4047* (2013.01); *A61B 5/4052* (2013.01); *A61B 6/032* (2013.01); *A61B 6/037* (2013.01); *A61B 6/461* (2013.01); *A61B 6/506* (2013.01); *A61B 8/0891* (2013.01); *A61B 18/06* (2013.01); *A61B 18/1492* (2013.01); *A61B 18/24* (2013.01); *A61B 34/25* (2016.02); *A61B 90/37* (2016.02); *G16H 50/50* (2018.01); *A61B 6/00* (2013.01); *A61B 6/12* (2013.01); *A61B 6/465* (2013.01); *A61B 8/085* (2013.01); *A61B 8/0841* (2013.01); *A61B 8/461* (2013.01); *A61B 34/20* (2016.02); *A61B 2017/320069* (2017.08); *A61B 2018/00351* (2013.01); *A61B 2018/00404* (2013.01); *A61B 2018/00434* (2013.01); *A61B 2018/00511* (2013.01); *A61B 2018/00577* (2013.01); *A61B 2018/0212* (2013.01); *A61B 2018/1435* (2013.01); *A61B 2018/1861* (2013.01); *A61B 2034/104* (2016.02); *A61B 2034/107* (2016.02); *A61B 2090/374* (2016.02); *A61B 2090/376* (2016.02); *A61B 2090/378* (2016.02); *A61B 2090/3735* (2016.02); *A61B 2090/3762* (2016.02); *A61B 2090/3954* (2016.02); *A61B 2090/3958* (2016.02); *A61B 2090/3966* (2016.02)

(58) Field of Classification Search
CPC ...... A61B 2090/3735; A61B 2034/104; A61B 2018/00511; A61B 2018/00434; A61B 2017/00577; A61B 2018/1861; A61B 2018/0212; A61B 2017/320069; A61B 34/10; A61B 5/407; A61B 4/4041; A61B 5/40; A61B 6/461; A61B 6/506; A61B 5/0066; A61B 5/4052; A61B 5/4047; A61B 5/201; A61B 8/0891; A61B 5/055; A61B 5/0536; A61B 90/37; A61B 34/25; A61B 18/24; A61B 18/06; A61B 18/1492; A61B 6/037; A61B 6/032; A61B 8/461; A61B 8/085; A61B 8/0841; A61B 2090/3966; A61B 6/00; A61B 2090/376; A61B 2018/00351; A61B 2034/107; A61B 6/465; A61B 34/20; A61B 6/12; A61B 2018/00404; A61B 2090/3958; G16H 50/50

See application file for complete search history.

(56) References Cited

U.S. PATENT DOCUMENTS

| | | | |
|---|---|---|---|
| 8,888,773 | B2 | 11/2014 | Chang et al. |
| 9,084,610 | B2 | 7/2015 | Goshgarian et al. |
| 9,168,094 | B2 | 10/2015 | Lee et al. |
| 2006/0004301 | A1 | 1/2006 | Kasevich |
| 2006/0142801 | A1 | 6/2006 | Demarais et al. |
| 2007/0129720 | A1 | 6/2007 | Demarais et al. |
| 2012/0116382 | A1 | 5/2012 | Ku et al. |
| 2013/0178910 | A1* | 7/2013 | Azamian ............... A61B 18/20 607/33 |
| 2014/0074076 | A1* | 3/2014 | Gertner ................. A61N 7/02 606/12 |
| 2018/0256248 | A1* | 9/2018 | Bae .................. A61B 18/1206 |

FOREIGN PATENT DOCUMENTS

| | | |
|---|---|---|
| WO | WO2012061153 | 5/2012 |
| WO | WO2012061161 | 5/2012 |
| WO | WO2012088482 | 6/2012 |
| WO | WO2013086461 | 6/2013 |
| WO | WO2015113027 | 7/2015 |
| WO | WO2015143372 | 9/2015 |
| WO | WO2017012907 | 1/2017 |

OTHER PUBLICATIONS

Brown, "Electrical impedance tomography (EIT): a review," Journal of Medical Engineering and Technology, vol. 27, No. 3, May/Jun. 2003, pp. 107-108.
Esler et al., "Renal Denervation: Not as Easy as it Looks," Science Translational Medicine, vol. 7, No. 285, Apr. 29, 2015, 4 pages.
Mahfoud et al., "Efficacy and Safety of Catheter-Based Radiofrequency Renal Denervation in Stented Renal Arteries," Circ Cardiovasc Interv. 2014; 7 :813-818.
Wolf et al., "Noninvasive assessment of lung volume: Respiratory inductance plethysmography and electrical impedance tomography." Crit Care Med 2005; vol. 33(3) Supplement.S163-S169.
Coulombe et al., "A Parametric Model of the Relationship Between EIT and Total Lung Volume." Physiol Meas 2005;26(4):401-411.
Zhang et al., "EIT Images of Ventilation: What Contributes to the Resistivity Changes?" Physiol. Meas., 2005, 26(2): S81-S92.
Brown, "Electrical impedance tomography (EIT): a review," Journal of Medical Engineering & Technology. 2003; 27:97-108.
U.S. Appl. No. 62/588,215, by Doug Hettrick et al, filed Nov. 17, 2017.
U.S. Appl. No. 15/965,687, by Coates et al., filed Apr. 27, 2018.
U.S. Appl. No. 15/965,692, by Coates et al., filed Apr. 27, 2018.
U.S. Appl. No. 15/965,675, by Coates et al., filed Apr. 27, 2018.

\* cited by examiner

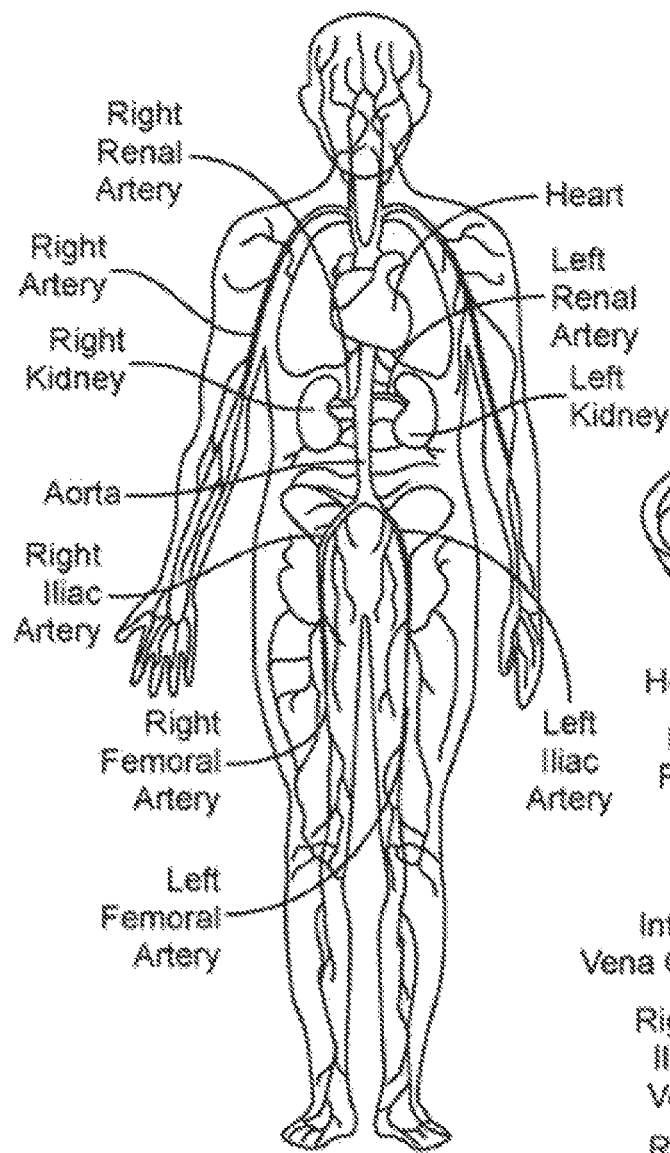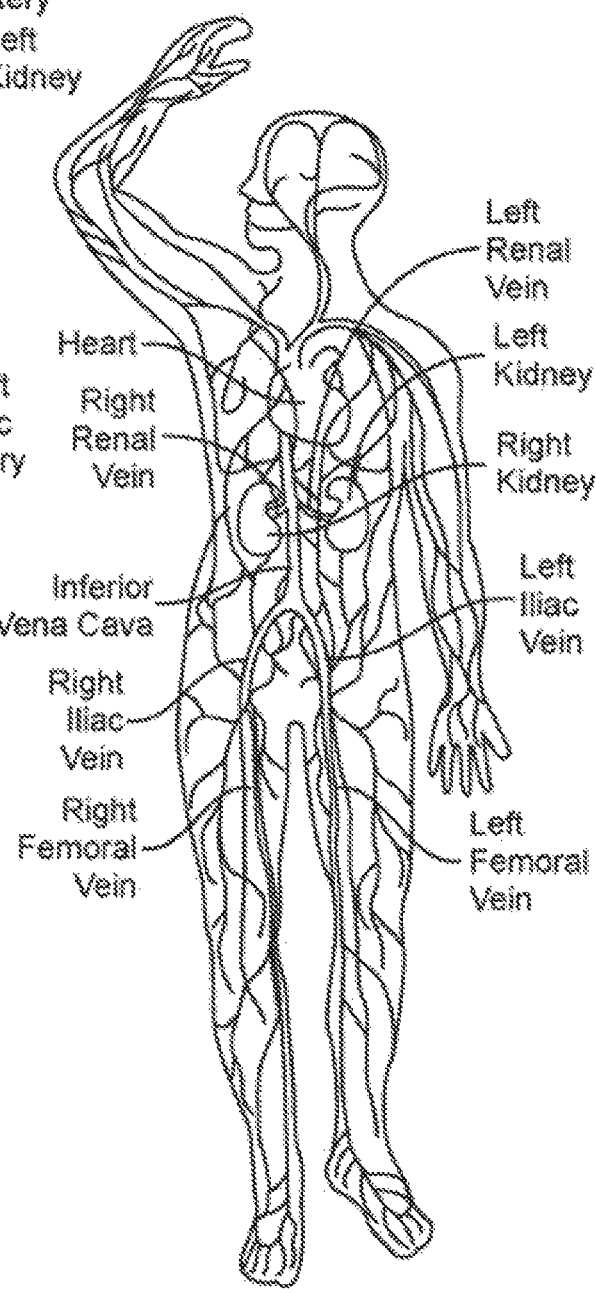
FIG. 13A
FIG. 13B

DENERVATION THERAPY

This application claims the benefit of U.S. Provisional Patent Application Ser. No. 62/621,351, entitled, "DENERVATION THERAPY" and filed on Jan. 24, 2018, the entire content of which is incorporated by reference herein.

TECHNICAL FIELD

The present disclosure relates to, in some examples, systems and techniques for denervation therapy.

BACKGROUND

Overstimulated or excessively active nerves may result in adverse effects to organs or tissue served by the respective nerves. For example, for some patients, heart, circulatory, or renal disease may be associated with pronounced cardio-renal sympathetic nerve hyperactivity. Stimulation of the renal sympathetic nerves can cause one or more of an increased renin release, increased sodium ($Na^+$) reabsorption, or a reduction of renal blood flow. The kidneys may be damaged by direct renal toxicity from the release of sympathetic neurotransmitters (such as norepinephrine) in the kidneys in response to high renal nerve stimulation. Additionally, the increase in release of renin may ultimately increase systemic vasoconstriction, aggravating hypertension. Such conditions may be mitigated by modulating the activity of overactive nerves.

SUMMARY

The present disclosure describes devices, systems, and techniques for determining one or more parameters of denervation therapy, which may also be referred to as neuromodulation therapy. The denervation therapy may include delivering electrical, chemical, light or laser, microwave, radiation, and/or thermal energy to a nerve in order to render the nerve inert, inactive, or otherwise completely or partially reduced in function. This complete or partial reduction in function may be temporary or permanent. Systems and techniques according to the disclosure may be used to estimate a volume of influence of a denervation stimulus delivered to a target nerve, and based on the volume of influence, to determine one or more parameters of denervation therapy. In some examples, the one or more parameters of denervation therapy determined based on the estimated volume of influence may be used to automatically control a medical device to deliver the denervation therapy to a patient. The volume of influence may be estimated based on a computer model generated from a digital reconstruction of a region of a patient, the digital reconstruction indicating parameters such as tissue types and relative locations. The volume of influence may be considered to be a volume within a predetermined region of a patient in which an applied denervation stimulus (also referred to herein as denervation stimulation) results in denervation, for example, by ablation or lesioning within the volume of influence. The volume of influence may indicate the effect of the denervation stimulus on tissue. Thus, the viability of nerves in the volume of influence may be reduced below a predetermined threshold, so that the nerves in the volume of influence exhibit reduced, substantially reduced, or substantially no activity. In some examples, the denervation therapy may result in lesioning of the target nerve while avoiding lesioning of a predetermined adverse-effect region, for example, a non-target non-nerve tissue.

In some examples, the disclosure describes an example technique that includes determining, by a processor, one or more tissue characteristics of tissue proximate a target nerve and a blood vessel, and determining, by the processor and based on the one or more tissue characteristics, an estimated volume of influence of denervation therapy delivered by a therapy delivery device disposed within the blood vessel. The technique further includes generating, by the processor, a graphical user interface. The graphical user interface includes a graphical representation of the tissue proximate the target nerve and the blood vessel and a graphical representation of the estimated volume of influence.

In some examples, the disclosure describes an example technique that includes determining, by a processor, a computer model based on a digital reconstruction of a region of a patient, where the region includes a target nerve and a blood vessel. The computer model defines a spatial representation of one or more tissue characteristics in the region. The example technique further includes determining, by the processor and based on the computer model, an estimated volume of influence of denervation therapy delivered by a therapy delivery device disposed within the blood vessel.

In some examples, the disclosure describes an example system that includes a memory configured to store one or more tissue characteristics of tissue proximate a target nerve and a blood vessel of a patient, and a processor coupled to the memory. The processor is configured to generate, based on the one or more tissue characteristics, an estimated volume of influence of denervation therapy delivered by a therapy delivery device disposed within the blood vessel. The processor is further configured to generate a graphical user interface. The graphical user interface includes a graphical representation of the tissue proximate the target nerve and the blood vessel and a graphical representation of the estimated volume of influence.

In some examples, the disclosure describes a non-transitory computer-readable medium that includes instructions that, when executed by at least one processor, cause the at least one processor to determine one or more tissue characteristics of tissue proximate a target nerve and a blood vessel of a patient, and determine, based on the one or more tissue characteristics, an estimated volume of influence of denervation therapy delivered by a therapy delivery device disposed within the blood vessel. The instructions further cause the at least one processor to generate a graphical user interface. The graphical user interface includes a graphical representation of the tissue proximate the target nerve and the blood vessel and a graphical representation of the estimated volume of influence.

In some examples, the disclosure describes an example system that includes means for determining one or more tissue characteristics of tissue proximate a target nerve and a blood vessel of a patient and means for determining, based on the one or more tissue characteristics, an estimated volume of influence of denervation therapy delivered by a therapy delivery means disposed within the blood vessel. The example system further includes means for generating a graphical user interface. The graphical user interface includes a graphical representation of the tissue proximate the target nerve and the blood vessel and a graphical representation of the estimated volume of influence.

In some examples, the disclosure describes an example technique that includes determining, by a processor, one or more tissue characteristics of tissue proximate a target nerve and a blood vessel of a patient. The example technique includes generating, by the processor and based on the one or more tissue characteristics, an estimated volume of influence of denervation therapy delivered by a therapy delivery device disposed within the blood vessel. The example technique includes controlling, by the processor and based on the estimated volume of influence, a surgical device to move the therapy delivery device to a predetermined location within the blood vessel.

In some examples, the disclosure describes an example system that includes a memory configured to store one or more tissue characteristics of tissue proximate a target nerve and a blood vessel of a patient, and a processor coupled to the memory. The processor is configured to determine one or more tissue characteristics of tissue proximate the target nerve and the blood vessel, and generate, based on the one or more tissue characteristics, an estimated volume of influence of denervation therapy delivered by a therapy delivery device disposed within the blood vessel. The processor is configured to control, based on the estimated volume of influence, a surgical device to move the therapy delivery device to a predetermined location within the blood vessel.

In some examples, the disclosure describes an example system that includes means for determining one or more tissue characteristics of tissue proximate a target nerve and a blood vessel of a patient, and means for generating, based on the one or more tissue characteristics, an estimated volume of influence of denervation therapy delivered by a therapy delivery means disposed within the blood vessel. The example system includes means for controlling, based on the estimated volume of influence, a movement means to move the therapy delivery means to a predetermined location within the blood vessel.

Clause 1: A method comprising: determining, by a processor, one or more tissue characteristics of tissue proximate a target nerve and a blood vessel of a patient; generating, by the processor and based on the one or more tissue characteristics, an estimated volume of influence of denervation therapy delivered by a therapy delivery device disposed within the blood vessel, and generating, by the processor, a graphical user interface, the graphical user interface comprising a graphical representation of the tissue proximate the target nerve and the blood vessel and a graphical representation of the estimated volume of influence.

Clause 2: The method of clause 1, wherein the estimated volume of influence comprises a lesion.

Clause 3: The method of clause 1 or 2, further comprising determining, by the processor and based on the estimated volume of influence, one or more therapy parameter values for denervation therapy delivery.

Clause 4: The method of clause 3, wherein the estimated volume of influence of the denervation therapy comprises a first estimated volume of influence of a first denervation therapy delivered by the therapy delivery device according to a first therapy program, the method further comprising: determining, by the processor, a second estimated volume of influence of a second denervation therapy delivered by the therapy delivery device according to a second therapy program, the second therapy program comprising at least one therapy parameter value different from a respective therapy parameter value of the first therapy program, wherein determining the one or more therapy parameter values for denervation therapy delivery comprises selecting one of the first therapy program or the second therapy program based on the respective first and second estimated volumes of influence.

Clause 5: The method of clause 3, wherein the estimated volume of influence comprises a lesion, and wherein determining the one or more therapy parameter values for denervation therapy delivery comprises selecting the one or more therapy parameter values determined to result in lesioning of the target nerve and avoiding lesioning of a predetermined adverse-effect region.

Clause 6: The method of clause 3, wherein the one or more therapy parameter values comprises at least one of an electrical signal parameter, a thermal signal parameter, an ultrasound signal parameter, a microwave signal parameter, an optical signal parameter, or a chemical dosage parameter.

Clause 7: The method of any one of clauses 3 to 6, further comprising controlling, by the processor, a medical device to deliver denervation therapy to the target nerve in accordance with the one or more therapy parameter values.

Clause 8: The method of any one of clauses 1 to 7, further comprising generating, by the processor and based on the estimated volume of influence, an indexed location of the therapy delivery device within the patient.

Clause 9: The method of clause 8, wherein the indexed location is a location of a therapy delivery element of the therapy delivery device relative to the blood vessel.

Clause 10: A method comprising: determining, by a processor, a computer model based on a digital reconstruction of a region of a patient, wherein the region comprises a target nerve and a blood vessel, and wherein the computer model defines a spatial representation of one or more tissue characteristics in the region; and generating, by the processor and based on the computer model, an estimated volume of influence of denervation therapy delivered by a therapy delivery device disposed within the blood vessel.

Clause 11: The method of clause 10, wherein the digital reconstruction is a three-dimensional (3D) digital reconstruction.

Clause 12: The method of clause 10 or 11, further comprising: subjecting, by the processor, the computer model to digital representations of a plurality of denervation stimuli, wherein each respective denervation stimulus of the plurality of denervation stimuli is delivered by the therapy delivery device in a respective pre-determined orientation and at a respective predetermined location along the blood vessel; and after subjecting the computer model to each denervation stimulus of the plurality of denervation stimuli, by the processor, generating a respective response state of the computer model to the respective denervation stimulus.

Clause 13: The method of clause 12, wherein the region comprises at least one non-target non-nerve tissue, further comprising, selecting, by the processor, at least one denervation stimulus in response to determining that the respective response state associated with the selected at least one denervation stimulus is indicative of viability of the non-target non-nerve tissue being greater than a threshold.

Clause 14: The method of clause 12, further comprising: selecting, by the processor, at least one denervation stimulus in response to determining that the respective response state associated with the selected at least one denervation stimulus is indicative of viability of the nerve being lower than a threshold; and determining, by the processor, a therapy program comprising the selected at least one denervation stimulus.

Clause 15: The method of clause 14, wherein the region comprises at least one non-target non-nerve tissue, and wherein the respective response state associated with the selected at least one denervation stimulus is indicative of viability of the non-target non-nerve tissue being greater than the threshold.

Clause 16: The method of any one of clauses 13 to 15, further comprising controlling, by the processor, a medical device to deliver the denervation therapy to the region of the patient according to the therapy program.

Clause 17: The method of clause 16, wherein the controlling the medical device comprises controlling a denervation stimulation generator based on the therapy program.

Clause 18: The method of any one of clauses 10 to 17, wherein the one or more tissue characteristics comprise at least one of electrical impedance, thermal conductivity, acoustic impedance, optical transmittivity, or chemical diffusivity.

Clause 19: The method of any one of clauses 10 to 18, wherein each denervation stimulus of the plurality of denervation stimuli independently comprises at least one of a radiofrequency (RF) stimulus, a thermal stimulus, a cryogenic stimulus, a microwave stimulus, an ultrasonic stimulus, an optical stimulus or a chemical stimulus.

Clause 20: The method of any one of clauses 10 to 19, further comprising generating the digital reconstruction of the region of the patient based on a medical image of the region of the patient.

Clause 21: The method of clause 20, wherein the medical image comprises at least one of a fluoroscopic image, a computer aided tomography (CAT) scan, a magnetic resonance imaging (MRI) image, a positron emission tomography (PET) scan, a tomographic image, an ultrasound image, or an optical image.

Clause 22: The method of any one of clauses 10 to 21, wherein the computer model comprises a finite element model.

Clause 23: The method of any one of clauses 10 to 22, wherein the at least one target nerve comprises a renal nerve and the blood vessel comprises a renal artery.

Clause 24: A system comprising: a memory configured to store one or more tissue characteristics of tissue proximate a target nerve and a blood vessel of a patient; and a processor coupled to the memory, wherein the processor is configured to: generate, based on the one or more tissue characteristics, an estimated volume of influence of denervation therapy delivered by a therapy delivery device disposed within the blood vessel, and generate a graphical user interface comprising a graphical representation of the tissue proximate the target nerve and the blood vessel, and a graphical representation of the estimated volume of influence.

Clause 25: The system of clause 24, wherein the estimated volume of influence comprises a lesion.

Clause 26: The system of clause 24 or 25, wherein the processor is configured to determine one or more therapy parameter values for denervation therapy delivery based on the estimated volume of influence.

Clause 27: The system of clause 26, wherein the estimated volume of influence of the denervation therapy comprises a first estimated volume of influence of a first denervation therapy delivered by the therapy delivery device according to a first therapy program, the processor being further configured to: determine a second estimated volume of influence of a second denervation therapy delivered by the therapy delivery device according to a second therapy program, the second therapy program comprising at least one therapy parameter value different from a respective therapy parameter value of the first therapy program, wherein the processor is configured to determine the one or more therapy parameter values for denervation therapy delivery by selecting one of the first therapy program or the second therapy program based on the respective first and second estimated volumes of influence.

Clause 28: The system of clause 26 or 27, wherein the estimated volume of influence comprises a lesion, and wherein the processor is configured to determine the one or more therapy parameter values for denervation therapy delivery by selecting the one or more therapy parameter values determined to result in lesioning of the target nerve and avoiding lesioning of a predetermined adverse-effect region.

Clause 29: The system of any one of clauses 26 to 28, wherein the one or more therapy parameter values comprises at least one of an electrical signal parameter, a thermal signal parameter, an ultrasound signal parameter, a microwave signal parameter, an optical signal parameter, or a chemical dosage parameter.

Clause 30: The system of any one of clauses 26 to 29, wherein the processor is further configured to control a medical device to deliver denervation therapy to the target nerve in accordance with the one or more therapy parameter values.

Clause 31: The system of any one of clauses 24 to 30, wherein the processor is further configured to generate, based on the estimated volume of influence, an indexed location of the therapy delivery device within the patient.

Clause 32: The system of clause 31, wherein the indexed location is a location of a therapy delivery element of the therapy delivery device relative to the blood vessel.

Clause 33: The system of clause 26, further comprising a therapy generator configured to generate, based on the one or more therapy parameter values, a denervation stimulus.

Clause 34: The system of clause 33, further comprising the therapy delivery device configured to be coupled to the therapy generator, wherein the therapy generator is configured to deliver the denervation therapy to the patient via the therapy delivery device.

Clause 35: The system of any of clauses 24 to 34, wherein the at least one therapy delivery device comprises at least one of an electrode, a radiofrequency (RF) probe, a thermal probe, a cryogenic probe, a microwave probe, an ultrasonic probe, an optical source, or a chemical injector.

Clause 36: The system of any one of clauses 24 to 35, further comprising an imaging system configured to image the target nerve and the blood vessel.

Clause 37: The system of clause 36, wherein the imaging system comprises at least one of a fluoroscopy system, a computer aided tomography (CAT) scan system, a magnetic resonance imaging (MRI) system, a positron emission tomography (PET) scan system, an electrical impedance tomography (EIT) system, an ultrasound system, or an optical imaging system.

Clause 38: The system of any one of clauses 24 to 37, wherein the target nerve comprises a renal nerve and wherein the blood vessel comprises a renal artery.

Clause 39: A non-transitory computer-readable medium, comprising instructions that, when executed, cause at least one processor to: determine one or more tissue characteristics of tissue proximate a target nerve and a blood vessel of a patient, generate, based on the one or more tissue characteristics, an estimated volume of influence of denervation therapy delivered by a therapy delivery device disposed within the blood vessel; and generate a graphical user interface comprising a graphical representation of the tissue proximate the target nerve and the blood vessel and a graphical representation of the estimated volume of influence.

Clause 40: The non-transitory computer-readable medium of clause 39, wherein the estimated volume of influence comprises a lesion.

Clause 41: The non-transitory computer-readable medium of clause 39 or 40, further comprising instructions, that, when executed, cause the at least one processor to determine, based on the estimated volume of influence, one or more therapy parameter values for denervation therapy delivery.

Clause 42: The non-transitory computer-readable medium of clause 41, wherein the estimated volume of influence of the denervation therapy comprises a first estimated volume of influence of a first denervation therapy delivered by the therapy delivery device according to a first therapy program, and wherein the non-transitory computer-readable medium further comprises instructions that, when executed, cause the at least one processor to: determine a second estimated volume of influence of a second denervation therapy delivered by the therapy delivery device according to a second therapy program, the second therapy program comprising at least one therapy parameter value different from a respective therapy parameter value of the first therapy program, wherein the instructions cause the processor to determine the one or more therapy parameter values for denervation therapy delivery by selecting one of the first therapy program or the second therapy program based on the respective first and second estimated volumes of influence.

Clause 43: The non-transitory computer-readable medium of clauses 41 or 42, wherein the estimated volume of influence comprises a lesion, and wherein the instructions cause the at least one processor to determine the one or more therapy parameter values for denervation therapy delivery by at least selecting the one or more therapy parameter values determined to result in lesioning of the target nerve and avoid lesioning of a predetermined adverse-effect region.

Clause 44: The non-transitory computer-readable medium of any one of clauses 41 to 43, wherein the one or more therapy parameter values comprises at least one of an electrical signal parameter, a thermal signal parameter, an ultrasound signal parameter, a microwave signal parameter, an optical signal parameter, or a chemical dosage parameter.

Clause 45: The non-transitory computer-readable medium of any one of clauses 41 to 44, further comprising instructions that, when executed, cause the at least one processor to control a medical device to deliver denervation therapy to the target nerve in accordance with the one or more therapy parameter values.

Clause 46: The non-transitory computer-readable medium of any one of clauses 39 to 45, further comprising instructions that, when executed, cause the at least one processor to generate, based on the estimated volume of influence, an indexed location of the therapy delivery device within the patient.

Clause 47: The non-transitory computer-readable medium of clause 46, wherein the indexed location is a location of a therapy delivery element of the therapy delivery device relative to the blood vessel.

Clause 48: The non-transitory computer-readable medium of any one of clauses 39 to 47, wherein the target nerve comprises a renal nerve and wherein the blood vessel comprises a renal artery.

Clause 49: A system comprising: means for determining one or more tissue characteristics of tissue proximate a target nerve and a blood vessel of a patient; means for generating, based on the one or more tissue characteristics, an estimated volume of influence of denervation therapy delivered by a therapy delivery means disposed within the blood vessel, and means for generating a graphical user interface comprising a graphical representation of the tissue proximate the target nerve and the blood vessel and a graphical representation of the estimated volume of influence.

Clause 50: The system of clause 49, further comprising means for determining, based on the estimated volume of influence, one or more therapy parameter values for denervation therapy delivery.

Clause 51: The system of clause 50, wherein the estimated volume of influence comprises a lesion, and wherein the means for determining one or more tissue characteristics comprises means for selecting the one or more therapy parameter values determined to result in lesioning of the target nerve and avoid lesioning of a predetermined adverse-effect region.

Clause 52: The system of clause 50, wherein the estimated volume of influence comprises a lesion, and wherein the means for determining one or more tissue characteristics comprises means for selecting the one or more therapy parameter values determined to avoid lesioning of a predetermined adverse-effect region.

Clause 53: The system of any one of clauses 50 to 52, wherein the target nerve comprises a renal nerve and wherein the blood vessel comprises a renal artery.

Clause 54: The system of any one of clauses 50 to 53, further comprising means for generating denervation therapy to a patient based on the one or more therapy parameter values.

Clause 55: A method comprising: determining, by a processor, one or more tissue characteristics of tissue proximate a target nerve and a blood vessel of a patient; generating, by the processor and based on the one or more tissue characteristics, an estimated volume of influence of denervation therapy delivered by a therapy delivery device disposed within the blood vessel; and controlling, by the processor and based on the estimated volume of influence, a surgical device to move the therapy delivery device to a predetermined location within the blood vessel.

Clause 56: The method of clause 55, further comprising determining, by the processor and based on the estimated volume of influence, one or more therapy parameter values for denervation therapy delivery.

Clause 57: The method of clause 56, wherein the estimated volume of influence comprises a lesion, and wherein determining the one or more therapy parameter values for denervation therapy delivery comprises selecting the one or more therapy parameter values determined to result in lesioning of the target nerve and avoiding lesioning of a predetermined adverse-effect region.

Clause 58: The method of clause 56, wherein the estimated volume of influence comprises a lesion, and wherein determining the one or more therapy parameter values for denervation therapy delivery comprises selecting the one or more therapy parameter values determined to avoid lesioning of a predetermined adverse-effect region.

Clause 59: The method of any one of clauses 56 to 58, further comprising causing, by the processor, the therapy delivery device to deliver denervation therapy to a patient based on the one or more therapy parameter values.

Clause 60: A system comprising: a memory configured to store one or more tissue characteristics of tissue proximate a target nerve and a blood vessel of a patient; and a processor coupled to the memory, wherein the processor is configured to: determine one or more tissue characteristics of tissue proximate the target nerve and the blood vessel; generate, based on the one or more tissue characteristics, an estimated volume of influence of denervation therapy delivered by a therapy delivery device disposed within the blood vessel; and control, based on the estimated volume of influence, a surgical device to move the therapy delivery device to a predetermined location within the blood vessel.

Clause 61: The system of clause 60, wherein the processor is further configured to determine, based on the estimated volume of influence, one or more therapy parameter values for denervation therapy delivery.

Clause 62: The system of clause 61, wherein the estimated volume of influence comprises a lesion, and wherein the processor is configured to determine the one or more therapy parameter values for denervation therapy delivery by selecting the one or more therapy parameter values determined to result in lesioning of the target nerve and avoiding lesioning of a predetermined adverse-effect region.

Clause 63: The system of clause 61, wherein the estimated volume of influence comprises a lesion, and wherein the processor is configured to determine the one or more therapy parameter values for denervation therapy delivery by selecting the one or more therapy parameter values determined to avoid lesioning of a predetermined adverse-effect region.

Clause 64: The system of any one of clauses 61 to 63, wherein the processor is further configured to control a medical device to deliver denervation therapy to a patient based on the one or more therapy parameter values.

Clause 65: The system of any one of clauses 60 to 64, further comprising a drive unit coupled to the processor and the therapy delivery device.

Clause 66: A system comprising: means for determining one or more tissue characteristics of tissue proximate a target nerve and a blood vessel of a patient; means for generating, based on the one or more tissue characteristics, an estimated volume of influence of denervation therapy delivered by a therapy delivery means disposed within the blood vessel; and means for controlling, based on the estimated volume of influence, a movement means to move the therapy delivery means to a predetermined location within the blood vessel.

Clause 67: The system of clause 66, further comprising means for determining, based on the estimated volume of influence, one or more therapy parameter values for denervation therapy delivery.

Clause 68: The system of clause 66, wherein the estimated volume of influence comprises a lesion, and wherein the means for determining one or more tissue characteristics comprises means for selecting the one or more therapy parameter values determined to result in lesioning of the target nerve and avoiding lesioning of a predetermined adverse-effect region.

Clause 69: The system of clause 66, wherein the estimated volume of influence comprises a lesion, and wherein the means for determining one or more tissue characteristics comprises means for selecting the one or more therapy parameter values determined to avoid lesioning of a predetermined adverse-effect region.

Clause 70: The system of any one of clauses 67 to 69, further comprising means for generating denervation therapy to a patient based on the one or more therapy parameter values.

Clause 71: The system of any one of clauses 66 to 70, further comprising a means for moving the therapy delivery means along the blood vessel.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein:

FIGS. 13A and 13B are, respectively, conceptual anatomic views of the arterial and venous vasculatures of a human.

DETAILED DESCRIPTION

Figures 1A, 1B:
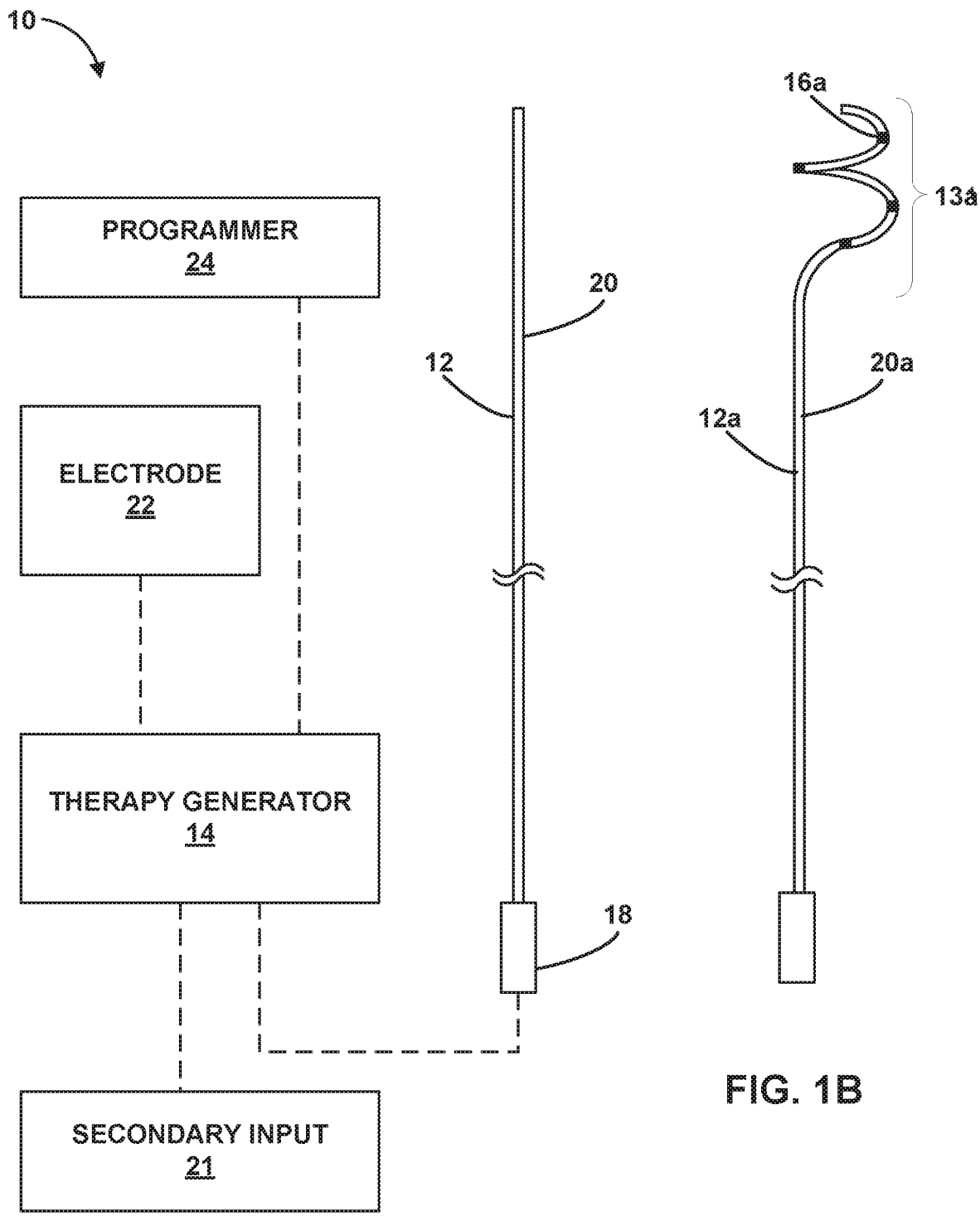
FIG. 1A is a schematic and conceptual illustration of an example system including a denervation therapy delivery device and a therapy generator.
FIG. 1B is a schematic and conceptual illustration of an example denervation therapy delivery device including at least one electrode.

Denervation therapy may be used to render a target nerve inert, inactive, or otherwise completely or partially reduced in function, such as by ablation or lesioning of the target nerve. In some examples, the target nerve may be a member of a nerve bundle, and denervation therapy may be used for ablation or lesioning of the nerve bundle. Following denervation, there may be a reduction or even prevention of neural signal transmission along the target nerve. Denervating an overactive nerve may provide a therapeutic benefit to a patient. For example, renal denervation may mitigate symptoms associated with renal sympathetic nerve overstimulation. Denervation therapy may include delivering electrical and/or thermal energy to a target nerve, and/or by delivering a chemical agent to a target nerve. In the case of renal denervation therapy, the denervation energy or chemical agents can be delivered, for example, via a therapy delivery device (e.g., a catheter) disposed in a blood vessel (e.g., the renal artery) proximate the renal nerve. It may be desirable to select one or more parameters of denervation therapy to achieve delivery of sufficient energy or chemical agent to denervate a target nerve, while minimizing or avoiding undue influence of non-target non-nerve tissue, non-target nerves, or one or more adverse-effects regions with the denervation energy or chemical agent. In other cases, it may be desirable to select one or more parameters of denervation therapy to minimize or avoid influence of non-target non-nerve tissue, non-target nerves, or one or more adverse-effects regions with the denervation energy or chemical agent.

The present disclosure describes devices, systems, and techniques for determining one or more parameters of denervation therapy using a computer model that takes into consideration patient-specific tissue characteristics and anatomy. The one or more parameters of denervation therapy can include, for example, an electrical signal parameter, a thermal signal parameter, an ultrasound signal parameter, a microwave signal parameter, an optical signal parameter, or a chemical dosage parameter, and may vary depending on the type of therapy delivered by a medical device to provide the denervation therapy. The one or more determined parameters of denervation therapy may be stored by a device, such as a medical device programmer or a medical device, as a therapy program, which may be used by the medical device to generate and deliver denervation therapy to a patient.

In some examples, an example system includes a memory configured to store one or more tissue characteristics of tissue proximate a target nerve and a blood vessel of a patient, and a processor coupled to the memory. The processor may be configured to determine one or more characteristics of tissue (also referred to herein as "tissue parameters") proximate a target nerve and a corresponding blood vessel (e.g., a blood vessel proximate the target nerve through which the target nerve may be accessed). The processor may be configured to generate, based on the one or more tissue characteristics and the characteristics of a therapy delivery device (e.g., number, size, and position of electrodes, position of openings for delivery of a chemical agent, or the like) an estimated volume of influence of denervation therapy delivered by a therapy delivery device disposed within a blood vessel. The estimated volume of influence may extend beyond the region or volume of tissue in which a stimulus is delivered. In some examples, an electric field or another denervation stimulus may extend within or pass through a first volume of tissue, but the volume of influence may extend beyond the first volume of tissue. For example, temperature of tissue beyond the first volume may rise beyond a denervation temperature or another denervation parameter threshold. In some examples, the processor may generate the estimated volume of influence using a computer model that defines a spatial representation of tissue, including respective tissue characteristics (e.g., thermal conductivity, electrical conductivity, density, and/or the like), in the region. The processor may be configured to generate a graphical user interface (GUI) that includes a graphical representation of the tissue proximate the target nerve and the corresponding blood vessel and a graphical representation of the estimated volume of influence.

In some examples, based on the estimated volume of influence, the processor may determine a therapy program that defines one or more therapy delivery parameters used to generate efficacious denervation therapy, e.g., a denervation stimulus. The denervation stimulus may be configured to cause the target nerve to exhibit a viability lower than a threshold, while leaving viability of non-target tissue greater than the threshold. A denervation stimulus may be electrical, thermal, chemical, optical, microwave, radiation, or any suitable type of stimulus that may affect the properties of tissue to which the stimulus is delivered.

In some examples, the processor may determine the effect of different therapy parameter values (a group of therapy parameter values that define the denervation stimuli delivered during a therapy session may be referred to as a therapy program or a set of therapy parameter values) on the volume of influence the volume and select a therapy program of the different therapy programs according to the corresponding volume of influence. For example, the processor may determine a first estimated volume of influence of a first denervation therapy delivered by the therapy delivery device according to a first therapy program. The processor may also determine a second estimated volume of influence of a second denervation therapy delivered by the therapy delivery device according to a second therapy program, where the second therapy program includes at least one therapy parameter value different from a respective therapy parameter value of the first therapy program. The processor may determine one or more therapy parameter values for denervation therapy by selecting one of the first therapy program or the second therapy program based on the respective first and second estimated volumes of influence. In other examples, the processor may select from any suitable number of therapy programs based on the corresponding volumes of influence.

In some examples, multiple therapy programs may provide efficacious results for a particular patient, e.g., due to similar targeting of the renal nerve or other nerve or target tissue site of interest by denervation stimuli. However, the result of the delivery of the denervation therapy according to the different therapy programs may differ from each other in one or more ways. For example, some therapy programs may define denervation stimuli that require more power to generate than one or more other therapy programs, such that some therapy programs may be more efficient (for example, in terms of power usage) than others. As another example, some therapy programs may result in lesioning of more non-target tissue than one or more other therapy programs. Thus, the therapy program selected by a processor of a device (e.g., a medical device programmer) or by a clinician may be selected not only based on the estimated lesioning of the target tissue site, but also based one or more other factors, such as the power consumed during a therapy session, the effect on a non-target tissue site, and the like. In some examples, a processor of a device may order a list of therapy programs based on one or more of these other factors (e.g., ascending or descending order based on power consumption, non-target tissue site volume affected by the therapy, or the like), and present the ordered list of therapy programs to a user via a display of the device. The processor may then select the one or more therapy programs for controlling delivery of the therapy to a patient in response to user input, or automatically based on the top one or more predetermined number of therapy programs in the ordered list.

In some examples, the processor may generate a plurality of therapy programs (which differ from each other by at least one therapy parameter value of a given therapy parameter), and determine a plurality of volumes of influence, each volume of influence of the plurality of volumes of influence being associated with a respective therapy program of the plurality of therapy programs. The processor may select a volume of influence of the plurality of volumes of influence, for example, at least one volume of influence that extends to a tissue of interest, while avoiding non-target sites, for example, predetermined adverse effect sites. Based on the at least one selected volume of influence, the processor may select a therapy program of the plurality of therapy programs. The selected therapy program may generate the at least one selected volume of influence at the target tissue site, such that the at least one volume of influence does not impact or extend into a non-target tissue site.

In some examples, the processor may determine the computer model based on a digital reconstruction of a region of a patient, where the region includes the target nerve and the corresponding blood vessel. The processor may, for example, generate the digital reconstruction using a patient-specific image of the region, generated using any suitable imaging modality.

Denervation of a target nerve may not be sufficiently predictable due to variations in the volume of influence for a given set of therapy delivery parameter values. The variations in volume of influence may be due to, for example, variations in tissue characteristics of tissue adjacent the target nerve or the blood vessel. For example, other nerves, bones, tendons, muscle, fat, lymph nodes, blood vessels, calcium deposits, and/or organs may be positioned in the same vicinity as a target nerve, and the tissue characteristics of this tissue may affect how denervation therapy affects the tissue. Example tissue characteristics include electrical impedance or conductivity (for example, isotropic or anisotropic conductivity), thermal conductivity, acoustic impedance, chemical diffusivity, or optical transmittance.

During delivery of renal denervation therapy, an indication of actual nerve location or technique for verifying actual nerve denervation may not be readily available. While some feedback may be available to a clinician, for example, by sensing one or more patient parameters (e.g., temperature and/or impedance in the vicinity of the therapy delivery device, vessel constriction, heart rate, blood flow, and/or patient motion), such feedback may not efficiently or effectively direct denervation therapy towards a target nerve and/or avoid lesioning a predetermined adverse-effect region. The predetermined adverse-effect region may include a non-target tissue, for example, non-nerve tissue or tissue otherwise not intended to be treated, but which may be susceptible to lesioning by a denervation stimulus. In some examples, the adverse-effect region may include fat, muscle, skeletal, or other tissue or organs, or nerves not intended to be denervated. A clinician may provide feedback to a medical device programmer that indicates the predetermined adverse-effect region, or the predetermined adverse-effect region may be prestored by the medical device programmer without the programming clinician's input. The computer model described herein may be used to better estimate and visualize the affect denervation therapy has on a target nerve and/or tissue proximate a target nerve, and, thereby generate a therapy program that better targets a target nerve and/or better avoids adversely affecting non-target tissue.

For example, a computing device may use the computer model to evaluate a plurality of denervation locations, and for each location, the computing device may determine denervation therapy parameter values (e.g., values for delivering an electrical, thermal, chemical, microwave, radiation, or optical stimulus, and, in the case of an electrical or thermal stimulus, the electrodes with which the stimulus is delivered) for achieving effective lesioning at that location. The computing device may then evaluate the entire data set, including therapy parameter values associated with the different locations, to determine a sub-set of locations (selected from the plurality of denervation locations) at which therapy may be delivered to achieve an overall denervation goal for the region of the patient. The therapy parameter values and corresponding locations may then be used to program a medical device configured to deliver the denervation therapy to the patient, and/or may be presented to a clinician via a user interface of the computing device as a recommended therapy regimen.

In some examples, the therapy parameter values determined using patient-specific tissue characteristics and anatomy may be used to perform guided denervation of a target nerve. For example, a denervation therapy delivery device (e.g., a catheter) may be navigated through a blood vessel, and positioned, oriented, and deployed manually by a clinician with the aid of a graphical user interface or automatically by a device, such as a computer-controlled robotic surgical device. The graphical user interface may include a graphical representation of tissue proximate a target nerve and the blood vessel and a graphical representation of an estimated volume of influence of therapy delivered by the therapy delivery device and in accordance with a particular therapy program.

The anatomy surrounding the renal artery of a human subject is relatively complex, and includes several different types of tissue having different thermal and/or electrical properties. Further, the location of a renal nerve relative to the renal artery may change along the length of the renal artery. For example, nerve bundles of the renal nerve may be further from the renal artery at a relatively more proximal location relative to the aortic artery. Closer to the kidney, the nerve bundles of the renal nerve may be closer to the renal artery. Further, certain types of tissues, such as arteries and veins, may act as electrical or thermal conductors, which can also affect the amount of energy needed to ablate the renal nerve.

As a result of the different tissue properties and the varying location of the renal nerve relative to the renal artery, therapy delivery parameters for efficacious renal denervation therapy may differ depending on the location along the renal artery at which the renal denervation therapy is delivered. For example, due to the changing distance between a renal nerve and renal artery, more energy may need to be applied to ablate or lesion the renal nerve when denervation therapy is delivered further from the kidney. However, it may be desirable to not set the energy so high as to adversely impact other regions of tissue, e.g., adverse-effect regions. Using the computer modeling techniques and estimated volumes of influence of renal denervation described herein, a processor of a medical device programmer may determine, based on the tissue characteristics, the energy level that may avoid certain regions of tissue (referred to herein as adverse-effects regions or non-target regions), and/or achieve denervation of the renal nerve.

Several of the factors adding to the complexity of selecting efficacious therapy parameter values for denervation therapy may be due at least in part to patient anatomy. For example, different patients may have different types of tissue closer to the renal artery, and the renal nerves may be located closer to the renal artery in some patients than in others. In some examples, a blood flow rate in a blood vessel, for example, a renal artery, may affect the volume of influence. For example, a higher blood flow rate may cause relatively faster thermal dissipation, leading to a smaller volume of influence for a given denervation stimulus than a volume of influence associated with a lower blood flow rate. The devices, systems, and techniques described herein that take into consideration patient-specific anatomy and tissue characteristics (including blood flow rate at or near a target tissue site) may help increase the efficacy, efficiency, or both, of denervation therapy delivery by a medical device compared to denervation therapy delivered in an ad hoc manner, without the aid of computer modeling described herein. The patient-specific anatomy can include, for example, the locations and relative arrangement of different anatomical structures of the patient (e.g., organs, blood vessels, target tissue sites, and the like), and the size of one or more blood vessels, which may correspond to a blood flow rate through the vessel, and, therefore, thermal and/or electrical conductivity of the blood vessel.

In some examples, example techniques may include pre-denervation imaging, digital reconstruction, and computer modeling of a patient region. A processor of a device, e.g., a medical device programmer, may generate a computer model based on a reconstruction of the patient region. The processor may determine denervation therapy parameter values based on estimated volume of influence determined using the computer model, and determine a denervation therapy program based on the denervation therapy parameters. For example, a processor may use images generated by pre-operative visualization to digitally reconstruct (for example, three-dimensional (3D)) anatomy around renal arteries. In some examples, the images may include a resolution sufficient to ascertain individual nerve bundles. In other examples, the resolution may be sufficient to ascertain relatively larger structures (for example, muscle, fat, lymph nodes, blood vessels, or gastrointestinal tract) as well as to measure size and location of different tissue sites, allowing the reconstruction of a relatively accurate 3D model of the region of the patient.

A processor may use the digital reconstruction to prepare a model, for example, a computer model or a bench model. The bench model may include a physical model of the region of the patient to be denervated, for example, a molded or sculpted model, a model generated using rapid prototyping, or an additively manufactured model. In some examples, the bench model may include different materials having different properties representing different types of tissue or anatomical features in the region of the patient. The bench model may include sensors at different locations to sense stimuli received at respective locations in the bench model from a denervation stimulus source. Based on the stimuli sensed at different locations in the bench model, which may estimate the lesion development at the respective location, a clinician may determine parameters for denervation therapy, including location and magnitude of denervation stimuli to be delivered at different locations.

Instead of, or in addition to the bench model, the clinician or a computing device may use a computer model of the patient region to determine the effects of different denervation stimuli and denervation locations. For example, the computer model may account for differences in tissue characteristics and inhomogeneities of different tissue types by incorporating electrical, thermal, and other appropriate properties associated with each tissue type. A processor may perform simulations of different therapy delivery programs using the computer model. For example, the processor may apply a simulated denervation stimulus at various locations along a blood vessel in the computer model, with variable amounts of denervation magnitude. The processor may monitor the effect of the denervation stimulus on the denervation target nerve and other non-target tissue adjacent the nerve in the model based on an estimated volume of influence of the denervation stimulus. The processor may thus use the computer model to generate therapy plan including a set of target denervation stimulus delivery locations, orientations, and magnitude to be delivered at that site, to achieve the targeted level of denervation.

The processor of the medical device may use the therapy plan (also referred to herein as a therapy program) to control denervation therapy provided to the patient. For example, a programmer may communicate a therapy program to a medical device including a therapy generator, where the therapy program may indicate the amount of energy to be delivered at one or more treatment locations along a blood vessel. For example, the therapy delivery device may include radiofrequency (RF) electrodes on a catheter introduced and advanced along a blood vessel of the patient. The location of the catheter may be provided to the therapy generator either via physician input, or through direct interaction by a processor receiving feedback from an imaging system (for example, a fluoroscopic system or some other tool for measuring location or orientation of the catheter/electrodes).

Even if the imaging resolution is not sufficient to find or identify particular nerves, for example, renal nerves, example systems and techniques according to the disclosure may be used to determine a maximum denervation stimulus that may be delivered at a location to create the largest lesion possible without lesioning non-target tissue. If the imaging resolution allows nerves to be identified, then example systems and techniques according to the disclosure may be used to determine suitable locations and therapy parameters to increase nerve denervation beyond a target threshold while maintaining non-target tissue lesioning lower than the threshold.

In contrast to some proposed renal denervation techniques in which a clinician controls delivery of RF energy via a therapy delivery device (for example, using unipolar or multipolar electrodes, on a balloon, basket or helix) according to an empirical procedure, the devices, systems, and techniques described herein may be used to determine therapy parameter values/settings for efficacious denervation therapy that are based on patient-specific anatomy. The parameters can include, for example, one or more orientations and/or locations (for example, anterior, posterior, or inferior superior) of a therapy delivery device within a patient, energy delivery parameters (e.g., frequency, duty cycle, and/or amplitude of an RF signal), and any other suitable parameters. For example, as described in further detail below, a processor of a medical device programmer, alone or with the aid of a clinician, may determine orientations and/or locations of a therapy delivery device within a patient or one or more energy delivery parameters that are expected to result in effective denervation of a target nerve, and substantially avoids adversely affecting other non-target tissue of the patient. Rather than introducing a catheter into the renal artery of patient according to a general set of rules that apply to a broad set of anatomical variations and delivering RF energy in accordance with those rules, the example devices, systems, and techniques described herein with respect to FIGS. 1A to 13B may provide renal denervation therapy that is generated based on with patient-specific anatomy. Such therapy may be more efficacious in that it may better deliver a denervation stimulus to a target nerve and/or avoid adversely impacting non-target tissue. In addition, in some cases, renal denervation therapy that is generated based on with patient-specific anatomy may result in a more efficient medical procedure because it may better distribute denervation stimuli to denervate a target nerve on a first pass through the blood vessel with the therapy delivery device. As discussed below, it may be desirable to reduce the amount of time of a denervation procedure in order to reduce adverse effects that may result from occlusion, if any, of one or more blood vessels during the medical procedure.

FIG. 1A is a schematic and conceptual illustration of an example system 10 including a denervation therapy delivery device 12 and a therapy generator 14. Denervation therapy delivery device 12 (also referred to as therapy delivery device 12) may include any device configured to deliver a denervation stimulus to a target nerve. The denervation stimulus may include, for example, at least one of a RF stimulus, a thermal stimulus, a cryogenic stimulus, a microwave stimulus, an ultrasonic stimulus, a microwave stimulus, a radiation stimulus, an optical stimulus, or a chemical stimulus, and therapy delivery device 12 may include one or more therapy deliver elements, such as, but not limited to, at least one of an electrode, a RF probe, a thermal probe, a cryogenic probe, a microwave probe, an ultrasonic probe, or a catheter configured to deliver a chemical agent to tissue of a patient. In some examples, one or more therapy delivery elements of therapy delivery device 12 may be incorporated into or mounted on a catheter 20.

For example, FIG. 1B is a schematic and conceptual illustration of an example denervation therapy delivery device 12a including at least one electrode. A plurality of electrodes 16a are shown in FIG. 1B and are referred to collectively as electrodes 16a. In the example shown in FIG. 1B, denervation therapy delivery device 12a includes four electrodes arranged in a spiral configuration. For example, electrodes 16a may be arranged approximately 90 degrees apart when looking at device 12a through an axis that runs through the center of the spiral. Electrodes 16a may be spaced any suitable distance from each other, and the spacing between electrodes 16a as well as other dimensions of therapy delivery device 12a may vary based on the particular application for which therapy delivery device 12a is intended to be used. For example, a maximum width of therapy delivery device 12a, e.g., along the spiral and taken in a direction orthogonal to a longitudinal axis of therapy delivery device 12a, may be 3 mm to 8 mm, although other widths are also contemplated. In some such examples, electrodes 16a may be coupled to generator 14 via an electrical lead, for example, an electrically conductive lead running through a catheter 20a.

In the examples shown in FIGS. 1A and 1B, therapy delivery device 12, 12a may include an elongated shaft having a handle 18 at a proximal region of a proximal portion of therapy delivery device 12, and a distal portion 20 (20a) extending distally relative to the proximal portion. Therapy delivery device 12, 12a further includes a therapeutic assembly or a treatment section at the distal portion 20. For example, as shown in FIG. 1B, therapy delivery device 12, 12a may include at least one electrode, or an array of two or more electrodes 16a, configured to be introduced into and advanced along a blood vessel, for example, a renal artery. In other examples, such as examples in which therapy delivery device 12 is configured to deliver a chemical agent to tissue, the treatment section can include one or more openings to a lumen of therapy delivery device 12, 12a, through which a chemical agent may be delivered.

Therapy delivery device 12, 12a may be configured to be delivered into a patient, e.g., a blood vessel of the patient, a low-profile configuration, such as the substantially straight configuration shown in FIG. 1A. Upon delivery to a target location within and along the blood vessel, therapy delivery device 12, 12a may be deployed into an expanded state (for example, a generally helical or spiral configuration), in which one or more therapy delivery elements of therapy delivery device 12, 12a, may contact the blood vessel. In the expanded state, therapy delivery device 12, 12a may deliver energy at a treatment site and provide therapeutically-effective electrically- and/or thermally-induced denervation. While a spiral or helical configuration is shown in the example of FIG. 1B, electrodes 16a may be alternatively disposed along a substantially straight and elongated therapy delivery device 12, as shown in FIG. 1A, or any other suitable configuration of electrodes, such as along an expandable basket, outwardly extending fingers, or the like.

In some examples, therapy delivery device 12 may be placed or transformed into the deployed state or arrangement via remote actuation, e.g., via an actuator, such as a knob, pin, or lever carried by handle 18. In other examples, however, therapy delivery device 12 may be transformed between the delivery and deployed states using other suitable mechanisms or techniques. For example, therapy delivery device 12 may include a shape memory material, such that therapy delivery device 12 is configured to assume the relatively low-profile delivery configuration under the force applied by an outer sheath, and upon withdrawal of the sheath, therapy delivery device 12 may automatically assume the deployed state.

A distal end of therapy delivery device 12 may terminate with, for example, an atraumatic rounded tip or cap. In addition, or instead, the distal end of the therapy delivery device 12 may be configured to engage another element of system 10 or therapy delivery device 12. For example, the distal end of therapy delivery device 12 may define a passageway for engaging a guidewire (not shown) for delivery of the treatment device using over-the-wire ("OTW") or rapid exchange ("RX") techniques.

Therapy delivery device 12 is configured to receive denervation energy from generator 14 and deliver the energy to adjacent tissue in the form of a denervation stimulus. Generator 14 may generate energy ultimately transmitted through one or more conductive leads to the electrodes 16a. In examples in which the denervation stimulus includes a non-electric stimulus, for example, a chemical agent, optical stimulus, or ultrasound, generator 14 may include a source of the non-electric stimulus (for example, a reservoir and pump for pumping predetermined amounts or concentrations of the chemical agent at predetermined flow rates, light or laser source, a microwave source, radiation source, or an ultrasound generator).

In some examples, generator 14 includes an electrical source, for example, an RF energy generator. Generator 14 is configured to generate a selected form and magnitude of energy for delivery to the target treatment site via therapy delivery device 12. Generator 14 can be electrically coupled to therapy delivery device 12 via a cable including one or more electrical conductors. At least one supply wire (not shown) may pass within a wall of therapy delivery device 12 or through a lumen in the therapy delivery device 12 to electrodes 16a, and transmit the denervation stimulus to electrodes 16a. In some examples, each electrode of electrodes 16a may be coupled to a respective supply wire. In other examples, however, two or more electrodes of electrodes 16a may be electrically coupled to the same supply wire.

A secondary input 21, for example, a foot pedal, may be connected (e.g., pneumatically connected or electrically connected) to generator 14 to allow the clinician to initiate, terminate and, optionally, adjust various operational characteristics of generator 14, including, but not limited to, power delivery. System 10 may also include a remote control device (not shown) that can be positioned in a sterile field and operably coupled to one or both of therapy delivery device 12 or generator 14. The remote control device may be configured to allow for selectively turning on/off electrodes 16*a*. In other examples, the remote control device may be built into handle 18.

System 10 may include a programmer 24, described in further detail with reference to FIG. 3. Generator 14 can be configured to receive one or more therapy parameter values with which generator generates and delivers denervation therapy via programmer 24. In some examples, generator 14 or programmer 24 may include one or more evaluation or feedback modules to provide feedback to the clinician before, during, and/or after denervation therapy.

In some examples, generator 14 is configured to deliver a denervation stimulus via an electrode 16*a* in a monopolar configuration. For example, system 10 may include an electrode 22 (or dispersive electrode) electrically connected to generator 14 and attached to the exterior of the patient. In other examples, generator 14 is configured to deliver a denervation stimulus via a plurality of electrodes 16*a*, 22 in a multipolar configuration.

Additionally, one or more sensors (not shown), such as one or more temperature (for example, thermocouple, thermistor, or the like), impedance, pressure, optical, flow, chemical or other sensors, may be located proximate to or within electrodes 16*a* and connected to one or more supply wires (not shown). For example, a total of two supply wires may be included, in which both wires could transmit the signal from the sensor and one wire could serve dual purpose and also convey the energy to electrodes 16*a*. Alternatively, a different number of supply wires may be used to transmit energy to electrodes 16*a*. The sensors may be used by a processor of therapy generator 14 to, for example, control delivery of denervation therapy, as described in PCT Application No. PCT/US2011/057756, published as PCT Publication No. WO 2012/061161 A1, herein incorporated in its entirety by reference.

Generator 14 may be part of a device or monitor that may include processing circuitry, such as a microprocessor, and a display. In some examples, functions described elsewhere with reference to programmer 24 may be performed by generator 14, and system 10 may not include a separate programmer. Thus, system 10 includes a memory (for example, in generator 14 or programmer 24) configured to store one or more tissue characteristics of tissue proximate a target nerve and a blood vessel of a patient, and a processor coupled to the memory. The processor is configured to determine one or more tissue characteristics of tissue proximate a target nerve and a blood vessel. The processor is configured to generate, based on the one or more tissue characteristics, an estimated volume of influence of denervation therapy delivered by therapy delivery device 12 disposed within the blood vessel. The processor is configured to generate a GUI that provides information to a clinician to help visualize denervation therapy, and determine the effects of different therapy delivery parameters. In some examples, the GUI includes a graphical representation of the tissue proximate the target nerve and the blood vessel and a graphical representation of the estimated volume of influence.

In some examples, a clinician may use the GUI as a guide to determine a series of target locations, and move therapy delivery device 12 along the series of target locations. The clinician may use a fluoroscopic display to verify movement of device 12 along the series of target locations. In some cases, the clinician may provide an input to the processor confirming correct device placement to the processor, at each of the series of locations, prior to generator 14 providing denervation stimulus at the particular location. The processor may cause a generator to deliver stimulation with appropriate ablation parameters for each location of the series of locations. The stimulation results in ablation or lesioning of tissue (e.g., a target nerve), but may not directly stimulate nerves or cardiac tissue of the patient. In some examples, the GUI or another display (for example, a fluoroscopic display) may include a graphical representation of one or more of the series of target locations, and may include not include a graphical representation of the estimated volume of influence.

Thus, systems and techniques according to the disclosure may constitute an improvement at least to the denervation therapy system 10 itself. For example, example systems and techniques according to the disclosure can provide more efficacious denervation therapy. In some examples, the denervation therapy may be delivered in less treatment time, for example, because of a relatively more even distribution of therapy delivery locations. Further, systems and techniques according to the disclosure may reduce or avoid the need for trial-and-error in the clinician's determination of placement, positioning, orientation, and denervation therapy parameters, for example, because the system may indicate suitable placement, positioning, orientation, and denervation therapy parameters to the clinician.

Figure 2:
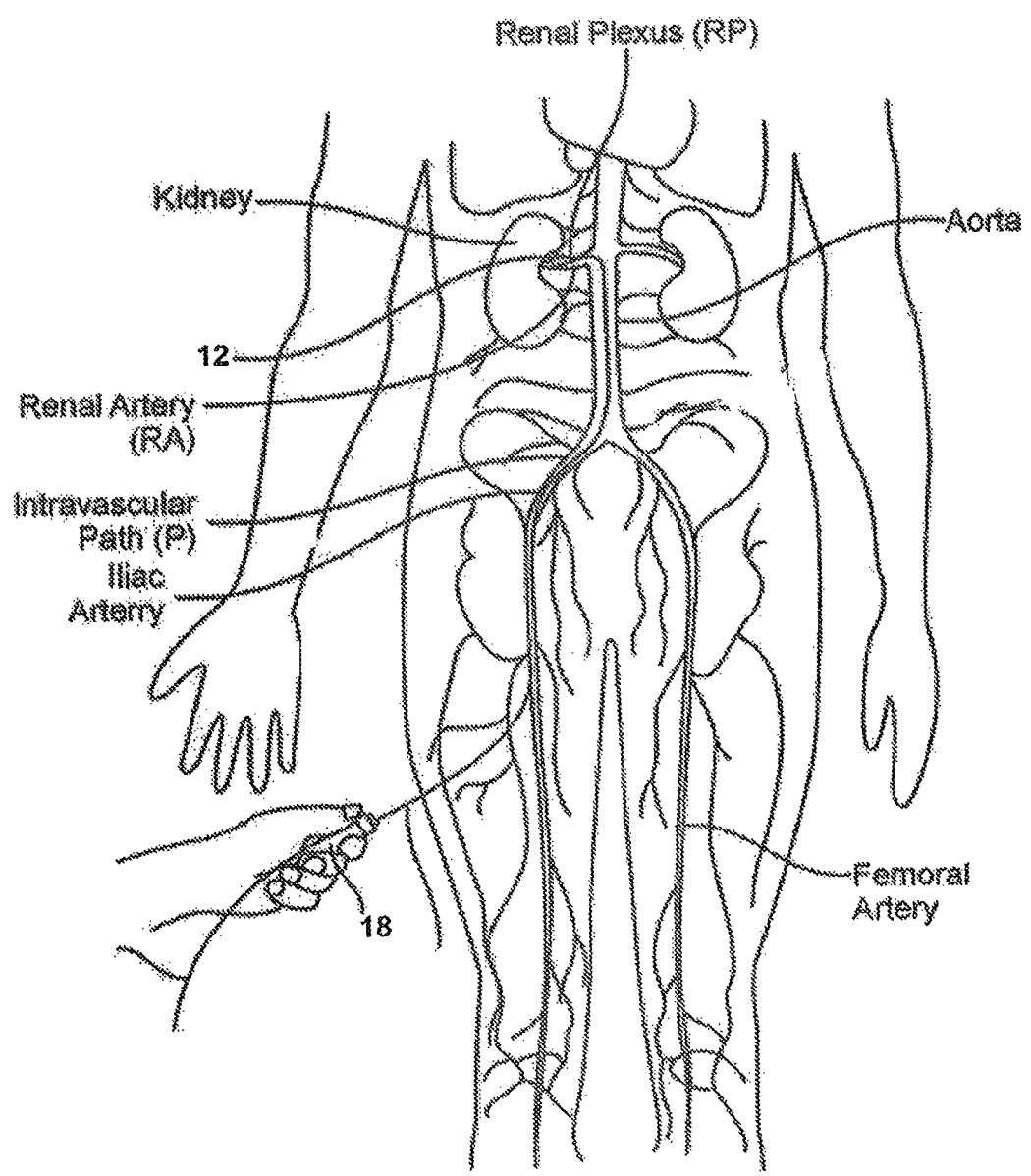
FIG. 2 is a schematic and conceptual illustration of deployment of the example system of FIG. 1A for delivering denervation therapy.

FIG. 2 is a schematic and conceptual illustration of deployment of example system 10 of FIG. 1A for delivering denervation therapy. Therapy delivery device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion of the shaft is exposed externally of the patient, near handle 18. By manipulating handle 18 and the external section of therapy delivery device 12 from outside the intravascular path P, the clinician may advance the distal portion 20 through the sometimes tortuous intravascular path P and remotely manipulate the distal portion 20.

Image guidance, for example, computed tomography (CT), fluoroscopy, intravascular ultrasound (IVUS), optical coherence tomography (OCT), or another suitable guidance modality, electrode impedance tomography (EIT), or combinations thereof, may be used to aid the clinician's manipulation. Further, in some examples, image guidance components (e.g., IVUS, electrode impedance tomography, or OCT) may be incorporated into the therapy delivery device 12 itself. After therapy delivery device 12 is positioned at a desired place in the renal artery RA, it can be radially expanded or otherwise deployed using handle 18 or other suitable means until electrodes 16*a* are in stable contact with the inner wall of the renal artery RA. The purposeful application of energy from electrodes 16*a* is then applied to tissue to induce one or more desired denervating effects on localized regions of the renal artery and adjacent regions of the renal plexus RP, which lay intimately within, adjacent to, or in close proximity to the adventitia of the renal artery RA. The purposeful application of the energy may achieve denervation along all or at least a portion of the renal plexus RP.

The denervating effects may generally depend on, at least in part, power, time, contact between electrodes 16*a* and the vessel wall, and blood flow through the vessel. The denervation effects may be accompanied by other effects, for example, thermal ablation, and non-ablative thermal alteration or lesioning (for example, via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal denervation effects may include altering the electrical signals transmitted in a nerve, for example, attenuating the electrical signals.

Exposure to thermal energy (e.g., heat) in excess of a body temperature of about 37° C., but below a temperature of about 45° C., may induce thermal alteration via moderate heating of the target neural fibers or of vascular structures that perfuse the target fibers. In examples in which vascular structures are affected, the target neural fibers are denied perfusion resulting in necrosis of the neural tissue. For example, this may induce nonablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected. A more detailed description of pertinent patient anatomy and physiology is described with reference to FIGS. 10 to 13B.

In some examples, electrodes 16a may be proximate to, adjacent to, or carried by (for example, adhered to, threaded over, wound over, and/or crimped to) a support structure. The proximal end of the support structure may be coupled to distal portion 20 of therapy delivery device 12 via a coupling (not shown). The coupling may be an integral component of the elongated shaft (i.e., may not be a separate piece) or the coupling may be a separate piece such as a collar (for example, a radiopaque band) wrapped around an exterior surface of the elongated shaft to secure the support structure to the elongated shaft. In other examples, however, the support structure may be associated with the elongated shaft using another arrangement and/or different features.

When multiple electrodes 16a are provided, electrodes 16a may deliver power independently (i.e., may be used in a monopolar fashion), either simultaneously, selectively, or sequentially, and/or may deliver power between any desired combination of the elements (i.e., may be used in a bipolar fashion). Furthermore, the clinician, generator 14, or programmer 24, optionally may choose which electrode(s) 16a are used for power delivery in order to form customized lesion(s) within the renal artery having a variety of predetermined shapes or patterns. The selection of the particular electrodes 16a with which a denervation stimulus is delivered to tissue is one example of a therapy delivery parameter value that programmer 24 can determine using the computer modeling techniques described herein.

The functioning of therapy delivery device 12 and generator 14 may be controlled by programmer 24 based on estimated volume of influence of denervation therapy. For example, programmer 24 may determine one or more therapy parameters for a therapy program for achieving predetermined levels of denervation in a target region of a patient.

Figure 3:
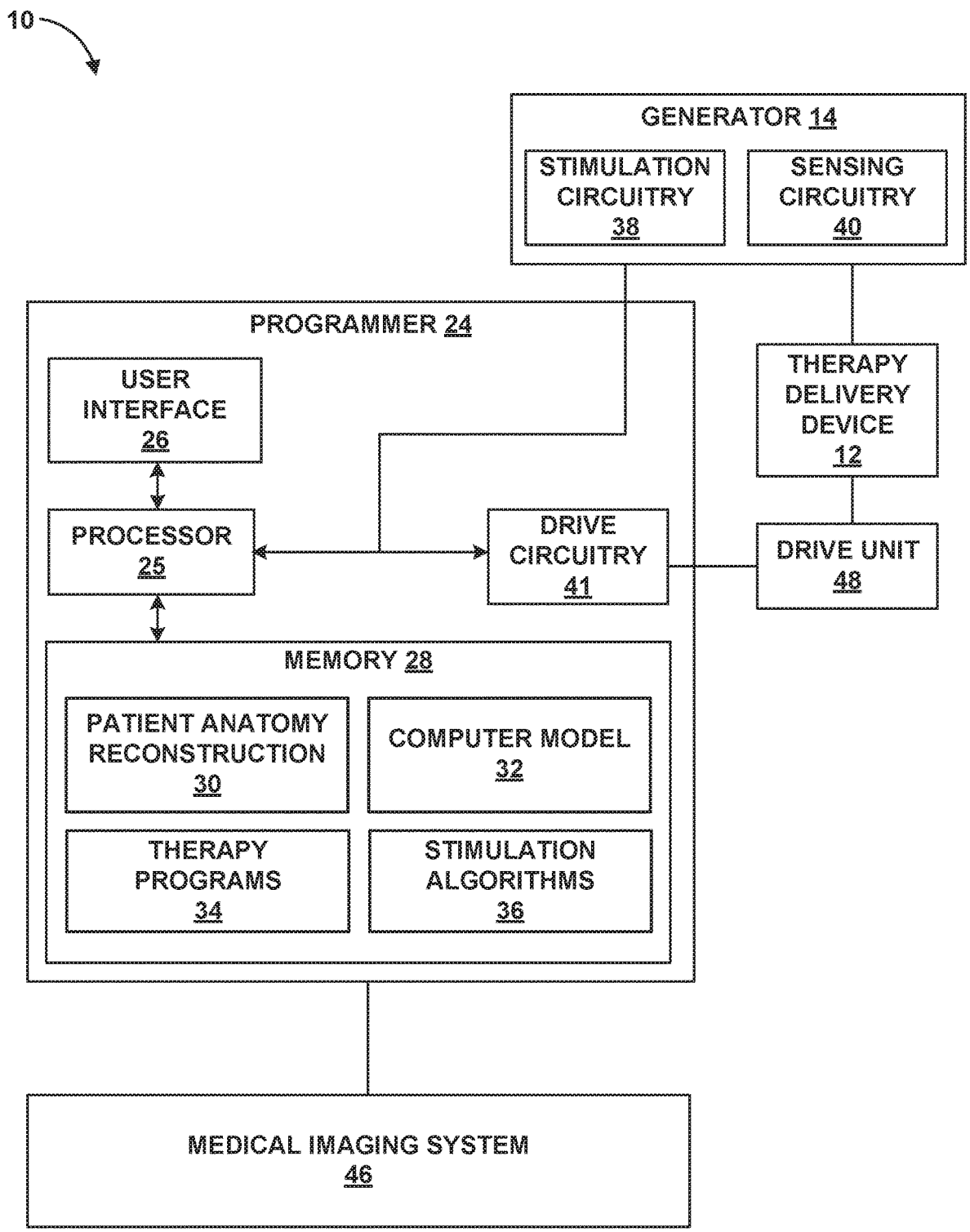
FIG. 3 is a schematic and conceptual illustration of an example programmer coupled to an imaging system and an example therapy delivery device.

FIG. 3 is a schematic and conceptual illustration of example programmer 24 coupled to a medical imaging system 46 and example therapy delivery device 12. While various circuitries, algorithms, modules, and functions are described with reference to programmer 24 of FIG. 3, in other examples, generator 14, or another medical device may include features and perform functions described with reference to programmer 24.

Programmer 24 includes a processor 25, a user interface 26, and a memory 28. Memory 28 includes computer-readable instructions that, when executed by processor 25, causes programmer 24 to perform various functions. Processor 25 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to processor 25 herein may be embodied as software, firmware, hardware or any combination thereof.

Memory 28 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 28 may store any suitable information, including patient identification information, and information for generating one or more therapy program with which generator 14 generates and delivers denervation therapy to a patient. For example, memory 28 may store one or more of patient anatomy reconstruction 30, computer model 32, therapy programs 34, stimulation algorithms 36, and operating instructions in separate memories within memory 28 or separate areas within memory 28.

Each therapy program 34 defines a particular program of therapy in terms of respective values for denervation stimulation parameters, such as the one or more electrodes 16a with which the stimulus is delivered to a patient, electrode polarity (if applicable), duty cycle, current or voltage amplitude, and/or frequency, or appropriate non-electrical parameters in examples in which the denervation stimulus includes non-electrical stimulus. Memory 28 may also store operating instructions with which processor 25 controls the operation of programmer 24, and may include instructions for measuring the impedance of electrodes 16a and/or determining placement and orientation of electrodes 16a along the blood vessel.

Generator 14 is configured to receive one or more therapy programs 34 from programmer 24, and apply the denervation therapy parameter values specified by the received one or more therapy programs 34, such as amplitude, duty cycle, and frequency, to generate a denervation stimulus. For example, generator 14 may control stimulation circuitry 38 to generate a denervation stimulation signal according to a particular therapy program, and deliver the denervation stimulation signal via therapy delivery device 12. Stimulation circuitry 38 may be electrically coupled to the one or more conductors of therapy delivery device 12 using any suitable technique. For example, generator 14 may include switching circuitry configured to switch the stimulation generated by stimulation circuitry 38 across different electrodes or generator 14 may include multiple energy sources to drive more than one electrode at one time.

In some examples, generator 14 may include sensing circuitry 40 coupled to therapy delivery device 12, for example, to receive electrical measurements, feedback, or signals, for example, impedance, which a processor of generator 14 may automatically control the delivery of a denervation stimulation signal via therapy delivery device 12.

In some examples, system 10 may include one or both of drive circuitry 41 or drive unit 48 ultimately coupled to therapy delivery device to control one or more of movement, location, or orientation of therapy delivery device 12 along the blood vessel in which therapy delivery device 12 is disposed. For example, drive unit 48 may include a stepper motor, a servo motor, or suitable motor, or magnetic rail, or any other suitable mechanism for advancing, retracting, rotating, and repositioning therapy delivery device 12 along the blood vessel. Drive circuitry 41 may control operation of drive unit 48, for example, by amplifying or sending control signals from processor 25 to drive unit 48. In some examples, drive circuitry 41 may receive feedback signals from drive unit 48 indicative of a current location or orientation of therapy delivery device 12, and freedom of or resistance to movement of therapy delivery device 12, and may send such feedback signals to processor 25 for ultimately controlling the movement and position of therapy delivery device 12.

A user, either a clinician or patient, may interact with processor 25 through user interface 26. User interface 26 may include a display, such as a liquid crystal display (LCD), light-emitting diode (LED) display, or other screen, to present information related to stimulation therapy, and buttons or a pad to provide input to programmer 24. In examples in which user interface 26 requires a 3D environment, the user interface may support 3D environments such as a holographic display, a stereoscopic display, an autostereoscopic display, a head-mounted 3D display, or any other display that is capable of presenting a 3D image to the user. Buttons of user interface 26 may include an on/off switch, plus and minus buttons to zoom in or out or navigate through options, a select button to pick or store an input, and pointing device, e.g. a mouse, trackball, or stylus. Other input devices may be a wheel to scroll through options or a touch pad to move a pointing device on the display. In some examples, the display may be a touch screen that enables the user to select options directly from the display screen.

In some examples, programmer 24 may include a telemetry module that may support wired or wireless communication between programmer 24 and generator 14 or another computing device under the control of processor 25. A clinician or another user may interact with programmer 24 to generate and/or select therapy programs 34 for delivery via therapy delivery device 12. In some examples, programmer 24 may allow a clinician to define target volumes of influence, and generate appropriate therapy delivery parameter values to achieve the desired volumes of influence. Programmer 24 may be used to present anatomical regions to the clinician via user interface 26, select therapy programs 34, generate new therapy programs 34 by manipulating computer model 32 or estimated volumes of influence presented on a GUI on user interface 26, and communicate the selected therapy programs 34 to the generator 14.

Programmer 24 may include a power source for delivering operating power to the components of programmer 24. The power source may include at least one battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries (e.g., nickel cadmium or lithium ion batteries) may be used. In addition, programmer 24 may be directly coupled to an alternating current source, such would be the case with some computing devices, such as personal computers. The power source may include circuitry to monitor power remaining within a battery. In this manner, user interface 26 may provide a current battery level indicator or low battery level indicator when the battery needs to be replaced or recharged. In some cases, the power source may be capable of estimating the remaining time of operation using the current battery.

In some examples, programmer 24 may be communicatively coupled to medical imaging system 46, or may otherwise receive one or more medical images of a patient from medical imaging system 46. Medical imaging system 46 may be configured to generate a medical image of a region of a patient that includes a target nerve (e.g., intended to be denervated) and, in some cases, a corresponding blood vessel. The corresponding blood vessel may be, for example, an artery or another blood vessel through which the target nerve may be accessed by a therapy delivery device. One or more medical images generated by medical imaging system 46 may be stored by programmer 24 in memory 28, or otherwise used by processor 25, to generate patient anatomy digital reconstruction 30. The medical image can be any medical image that provides sufficient resolution for identifying the tissue regions to avoid (for example, particular muscles, lymph nodes, other blood vessels veins/arteries, the kidney itself, the digestive tract, or other anatomical features or tissue).

In some cases, memory 28 of programmer 24 or another device (e.g., a remote device) may store a plurality of medical images of a patient, which can be, for example, a plurality of medical images of the same or nearly the same region of the patient. In some cases, if there has been a relatively large gap of time between denervation therapy sessions (e.g., on the order of weeks, months, or even years), a clinician may elect to use medical imaging system 46 to generate one or more updated medical images of the patient or otherwise obtain updated medical images of the patient, and update the one or more therapy programs used by generator 14 based on the one or more updated medical images. In some examples, the plurality of medical images may include any suitable available medical images of the patient region, for example, images obtained of the patient region obtained for a therapy other than denervation therapy. There may be changes to a particular patient's anatomy and/or tissue characteristics over time, such as due to weight gain, weight loss, or the like.

In some examples, medical imaging system 46 includes at least one of a fluoroscopy system, a computer aided tomography (CAT) scan system, a magnetic resonance imaging (MRI) system, a positron emission tomography (PET) scan system, an electrical impedance tomography (EIT) system, an ultrasound system, or an optical imaging system. In some examples, EIT may be used to identify the gross location of extravascular structures like nerves, fat, kidney veins, and the like. In some examples, locating these or other structures in three-dimensional space, for example, by EIT, may improve digital reconstruction 30 or computer model 32. Processor 25 may be configured to develop computer model 32 based on patient anatomy reconstruction 30. In some examples, computer model 32 includes a finite element model. In some examples, digital reconstruction 30 includes a three-dimensional (3D) reconstruction. Processor 25 may use one or both of digital reconstruction 30 or computer model 32 to determine an estimated volume of influence of denervation therapy, and determine one or more therapy programs 34 based on the estimated volume of influence, as described with reference to FIGS. 4, 6, and 7. Processor 25 may further also be used to deliver and monitor delivery of denervation therapy by generator 14 based on therapy programs 34, as described with reference to FIGS. 4, 6, and 7.

Figure 4:
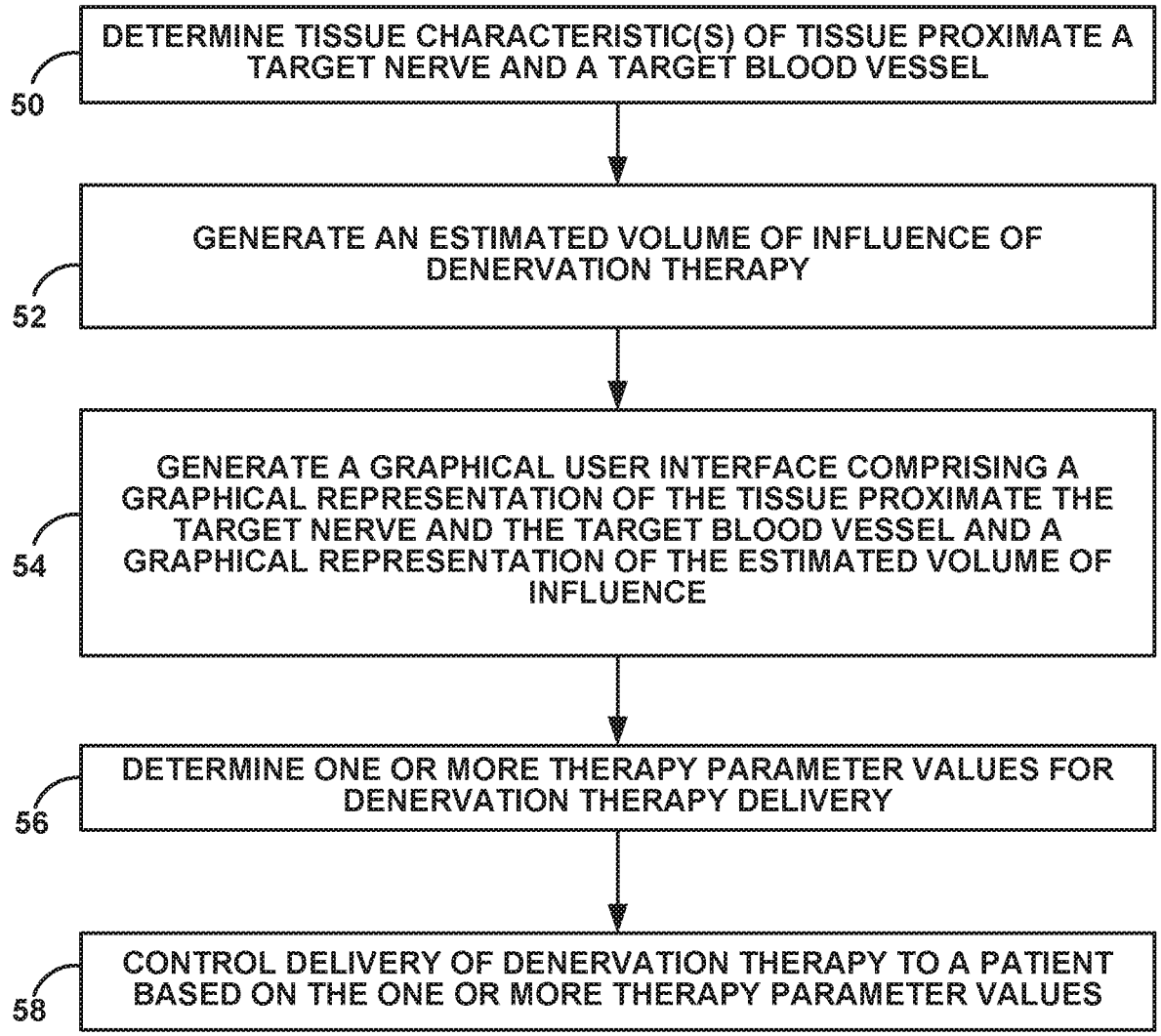
FIG. 4 is a flow diagram illustrating an example technique for delivering denervation therapy.

FIG. 4 is a flow diagram illustrating an example technique for delivering denervation therapy. The example techniques of FIGS. 4 to 7 are described with reference to the example systems of FIGS. 1A, 1B, 2, and 3. However, example techniques of FIGS. 4 to 7 may be performed using any suitable systems or devices. In some examples, the example technique of FIG. 4 includes determining, by processor 25, one or more tissue characteristics of tissue proximate a target nerve and a blood vessel (50). The tissue characteristics may include, but are not limited to, one or more of electrical impedance, thermal conductivity, acoustic impedance, chemical diffusivity, optical transmittivity, or density of tissue. The tissues may include blood, muscle, fat, nerve, fluid, bone, kidney, calcium deposits or any suitable tissue. In some examples, processor 25 may determine the tissue characteristics by at least generating a computer model 32 based on digital reconstruction 30 including the target nerve and blood vessel, as described with reference to FIG. 5.

Processor 25 may generate, based on the one or more tissue characteristics, at least one estimated volume of influence of denervation therapy delivered according to one or more respective therapy programs via therapy delivery device 12 disposed within the blood vessel (52). For example, based on the thermal and electrical conductivity associated with different tissue types identified from computer model 32 of the region of the patient, processor 25 may determine the volumetric reach to which energy or denervation stimulation may be electrically or thermally conducted from electrodes 16a (or generally from a location and orientation of a therapy delivery element of therapy delivery device 12, 12a). As an example, processor 25 may determine the estimated propagation of RF signals having predetermined frequencies and amplitudes, and the estimate propagation of thermal waves, based on tissue properties such as conductivities and densities. As another example, based on chemical diffusivity of tissue indicated from computer model 32 of the region of the patient, processor 25 may determine the volumetric reach of chemical stimulation resulting from delivery of a chemical agent delivered by therapy delivery device 12, 12a.

In some examples, computer model 32 may account for blood flow rates in one or more blood vessels in a region of the patient. For example, a blood flow rate in a blood vessel, for example, a renal artery, may affect the volume of influence resulting from delivery of a stimulus by therapy delivery device 12. For example, a higher blood flow rate may cause relatively faster thermal dissipation, leading to a smaller volume of influence for a given denervation stimulus than a volume of influence associated with a lower blood flow rate. In some examples, computer model 32 may include blood flow rates at or near a target tissue site, which may help increase the efficacy, efficiency, or both, of denervation therapy delivery by a therapy delivery device 12, 12a compared to denervation therapy delivered in an ad hoc manner, without the aid of computer model 32. The patient-specific anatomy can include, for example, the locations and relative arrangement of different anatomical structures of the patient (e.g., organs, blood vessels, target tissue sites, and the like), and the size of one or more blood vessels, which may correspond to a blood flow rate through the vessel, and, therefore, thermal and/or electrical conductivity of the blood vessel.

In some examples, computer model 32 may also account for the degree of contact between electrodes or other energy delivery elements of therapy delivery device 12, 12a and tissue of the patient in order to estimate the volume of influence of one or more denervation stimuli.

Processor 25 may use any suitable technique to determine the estimated volume of influence, including, but not limited to, a finite element model or another algorithm that numerically represents how different stimuli affect different types of tissue. Regardless of whether the stimulus is an electrical, thermal, chemical, optical, or other type of stimulus, the estimated volume of influence may be indicative of the extent of denervation stimulus and may be indicative of viability of nerve and non-nerve tissue subjected to the denervation stimulus. For example, processor 25 may determine that no lesions may be formed in tissue outside the estimated volume of influence, while lesions may be formed within the estimated volume of influence. Thus, in some examples, the estimated volume of influence includes a lesion, for example, a denervating lesion. In some examples, one or more volumes of influence or lesions may extend circumferentially about a vessel, for example, surrounding more than about 180° about an axis along the vessel, or surrounding more than about 270° about the axis, or surrounding more than about 300° about the axis, or substantially surrounding 360° about the vessel. In some examples, a periphery of the vessel may have a substantially circular cross-section normal to the axis. In other examples, the cross-section may be non-circular, for example, any closed curved. In some examples, the volumes of influence or lesions may extend along a substantially circular path about the axis. In other examples, the volumes of influence or lesions may extend along a non-circular path, a closed path, or an open path (for example, a helical path) about the axis.

In some examples, processor 25 may determine two or more estimated volumes of influence based on respective therapy programs. For example, processor 25 may generate a first estimated volume of influence of a first denervation therapy delivered by therapy delivery device 12 according to a first therapy program of therapy programs 34, and determine a second estimated volume of influence of a second denervation therapy delivered by therapy delivery device 12 according to a second therapy program of therapy programs 34. The second therapy program includes at least one therapy parameter value different from a respective therapy parameter value of the first therapy program.

In some examples, processor 25 may determine multiple therapy programs that each provides efficacious results for a particular patient, e.g., due to similar targeting of the renal nerve or other nerve or target tissue site of interest by denervation stimuli. However, the result of the delivery of the denervation therapy according to the different therapy programs may differ from each other in one or more ways. For example, some therapy programs may define denervation stimuli that require more power to generate than one or more other therapy programs, such that some therapy programs may be more efficient (for example, in terms of power usage) than others. As another example, some therapy programs may result in lesioning of more non-target tissue than one or more other therapy programs. Thus, processor 25 may select a therapy program not only based on the estimated lesioning of the target tissue site, but also based one or more other factors, such as the power consumed during a therapy session, the effect on a non-target tissue site, and the like. In some examples, processor 25 may order a list of therapy programs based on one or more of these other factors (e.g., ascending or descending order based on power consumption, non-target tissue site volume affected by the therapy, or the like), and present the ordered list of therapy programs to a user via a display of user interface 26.

Processor 25 may then select the one or more therapy programs for controlling delivery of the therapy to a patient in response to a user input, or automatically based on the top one or more predetermined number of therapy programs in the ordered list.

In some examples, processor 25 may generate a plurality of therapy programs (which differ from each other by at least one therapy parameter value of a given therapy parameter), and determine a plurality of volumes of influence, each volume of influence of the plurality of volumes of influence being associated with a respective therapy program of the plurality of therapy programs. Processor 25 may determine a volume of influence of the plurality of volumes of influence, for example, at least one volume of influence that extends to a tissue of interest, while avoiding non-target sites, for example, predetermined adverse effect sites. Based on the at least one volume of influence, processor 25 may select a therapy program of the plurality of therapy programs for delivering the denervation therapy to the patient. Processor 25 may control generator 14 to generate and deliver denervation therapy according to the therapy delivery parameters defined by the selected therapy program, generating the at least one volume of influence at the target tissue site, such that the at least one volume of influence does not impact or extend into a non-target tissue site.

In some examples, processor 25 may generate a plurality of therapy programs (which differ from each other by at least a location of volume of influence along a vessel). For example, processor 25 may generate a plurality of therapy programs delivered at a plurality of locations along the vessel, for example, six, nine, twelve, or any suitable number of locations along the length of the vessel. Processor 25 may determine a plurality of volumes of influence, each volume of influence of the plurality of volumes of influence associated with a respective location of the locations along the vessel. In some examples, two or more volumes of influence along the vessel may overlap in volume. In some examples, processor 25 may select a therapy program that achieves a relatively simple pattern of therapeutic influence, for example, ablation, along the vessel. For example, the simple pattern may be the most efficient with respect to power usage or duration of a therapy session, or the easiest for a clinician to deliver, or may result in relatively lowest adverse effects along the vessel in non-target tissue sites along the vessel, or otherwise result in a given pattern of therapy delivery along the vessel. In some examples, processor 25 may select a therapy program that generates a pattern of volumes of influences along the vessel for a given therapy delivery device, for example, a given type or configuration or orientation of catheter or electrodes along the therapy delivery device. In some examples, the given therapy delivery device may include a catheter defining a spiral or helical portion, and three, four, or more electrodes or any suitable therapy delivery elements simultaneously delivering therapy along the spiral or helical portion.

In some examples, processor 25 may select a therapy program generating different volumes of influence, for example, extending to different geometric volumes, at different locations along the vessel. The particular volumes of influence at specific locations may correspond to, for example, the location of the target tissue site (e.g., a renal nerve) relative to the therapy delivery device. In some examples, the therapy program may generate a smaller volume of influence at one or more locations along the vessel, and a larger volume of influence along other locations along the vessel. In some examples, the volumes of influence may progressively increase in volume, or progressively decrease in volume, along the vessel.

In some examples, processor 25 may select a plurality of therapy programs, each therapy program of the plurality of therapy programs associated with a location of the different locations along the vessel. Different therapy programs of the plurality of therapy programs may differ in one or more therapy parameters at different locations. In some examples, the respective magnitudes of therapy parameters of respective therapy programs may progressively increase, or progressively decrease, along the vessel.

In some examples, processor 25 generates GUI 26 (54), which may include a graphical representation of the tissue proximate the target nerve and the blood vessel and a graphical representation of the estimated volume of influence. This GUI 26 may provide a clinician with the information to relatively quickly ascertain the therapeutic effects of a particular therapy program on a particular patient in ways that existing renal denervation therapy programming that do not provide such patient-specific modeling may not allow.

In addition to or instead of generating GUI 26, processor 25 may determine, based on the estimated volume of influence, one or more therapy parameter values for efficacious denervation therapy delivery (56). For example, processor 25 may select one or more of the modeled therapy programs 34 based on the resulting estimated volume of influence (52). The therapy parameter values may include, for example, at least one of an electrical signal parameter, a thermal signal parameter, an ultrasound signal parameter, a microwave signal parameter, or a chemical dosage parameter. In some examples, the therapy parameter values can include, for example, respective locations within the patient for the delivery of a denervation stimulus. Processor 25 may select the one or more therapy parameter values using any suitable criterion or criteria. For example, in some cases, processor 25 determines the one or more therapy parameter values by at least selecting the one or more therapy parameter values (or therapy programs) determined to result in lesioning of the target nerve and avoiding lesioning of a predetermined adverse-effect region. In other examples, processor 25 determines the one or more therapy parameter values by at least selecting the one or more therapy parameter values (or therapy programs) determined to avoid lesioning of a predetermined adverse-effect region, without necessarily resulting in estimated lesioning of the target nerve.

In examples in which processor 25 generates estimated volumes of influence, processor 25 determines the one or more therapy parameter values for denervation therapy delivery by at least selecting a subset (e.g., one or more) of the plurality of modeled therapy programs. For example, in the example above in which processor 25 generates estimated volumes of influence for each of a first therapy program and the second therapy program based on the respective first and second estimated volumes of influence, processor 25 may select the therapy program associated with the volume of influence that encompasses a denervation target nerve, and/or results in a volume of influence that avoids lesioning of a predetermined adverse-effect region (for example, a tissue or organ in which lesioning is not sought).

In some examples, processor 25 may generate a GUI 26 that orders the therapy programs 34 based on determined efficacy (e.g., resulting in lesioning of a target nerve and/or avoiding lesioning of an adverse-effect region, or a clinician may otherwise select one of therapy programs 34. For example, processor 25 may associate each stored therapy program 34 with a numerical score based on the associated estimated volumes of influence, the score indicating, for example, the amount of overlap of the estimated volume of influence with the target nerve and/or amount of overlap with an adverse-effect region. Processor 25 may then order the therapy programs 34 in ascending or descending order based on scores. A clinician may then quickly review the ordered list of therapy programs to determine which one or more therapy programs should be used to program generator 14.

In some examples, processor 25 may controls generator 14 to generate and deliver denervation therapy to a patient based on the determined one or more therapy parameter values 34 (58). For example, processor 25 may transmit one or more selected therapy programs 34 to generator 34 via wired or wireless communication, or directly controls stimulation circuitry 38 to generate and deliver the denervation therapy based on a selected therapy program 34.

In some examples, the example technique further includes generating, by processor 25 and based on the estimated volume of influence, an indexed location of therapy delivery device 12 within the patient, and associating the indexed location with a particular therapy program. For example, the indexed location may be a location along the blood vessel (or alone a shaft of therapy delivery device 12), and the indexed location may be a location of a therapy delivery element (for example, electrodes 16a) of therapy delivery device 12 relative to the blood vessel or another anatomical landmark or landmark on therapy delivery device 12. The indexed locations may be used to determine the extent to which therapy delivery device 12 has advanced within the blood vessel or otherwise the proximity of one or more therapy delivery elements (for example, electrodes 16a) of therapy delivery device 12, 12a. For example, GUI 26 or another display may include a graphical representation of one or more index locations. In some examples, GUI 26 or another display may include a graphical representation of one or more index locations, without including a graphical representation of volumes of influence. In some examples, drive unit 48 may advance or retract therapy delivery device 12, 12a along the blood vessel by monitoring the index locations, for example, index locations on therapy delivery device 12 that may be ascertainable external to the body vessel.

Any suitable technique may be used by a processor of drive unit 48 to control the position of therapy delivery device 12. For example, drive unit 48 may include an optical unit that monitors visible markers on therapy delivery device 12 to determine the relative position of therapy delivery device 12 relative to an entry point into the patient. As another example, therapy delivery device 12 may include magnetic markers, and drive unit 48 may determine the relative position of therapy delivery device 12 (e.g., relative to programmer 24) using the magnetic markers, e.g., the magnitude of a magnetic field generated by the magnetic markers and sensed by a sensor of drive unit 48. In some examples, therapy delivery device 12 may include radiopaque or x-ray markers detectable under fluoroscopy, which the clinician or drive unit 48 may align with predetermined registration markers overlaid on a display of the fluoroscopic or other medical image. The radiopaque markers overlaid on a displayed medical image may enable the clinician to manually assess positioning of therapy delivery device 12.

In some examples, processor 25 may generate a GUI that includes an image, such a fluoroscopic image of the region of the patient, and may overlay markers on the image to show a clinician where the indexed locations are located relative to patient anatomy. Processor 25 may overlay one marker at a time to help guide the clinician to a next location for delivery of a denervation stimulus, or may overlay a plurality of markers at a time. For example, the clinician may compare the overlaid markers with markers indicative of the indexed locations, for example, radiopaque markers on therapy delivery device 12. A clinician may use this information to manually guide therapy delivery device 12 to different locations within the patient during a medical procedure. In other examples, processor 25 may communicate with a fluoroscopy imaging system or another imaging system, which may then overlay the one or more markers on a medical image of the patient similar to the foregoing example.

In some examples, a target nerve or nerve bundle may not be perceptible by imaging. In some such examples, processor 25 or a clinician may attempt to lesion a target region in which the presence of nerves may be suspected or predicted, without causing an adverse effect on a non-target tissue. In some such examples, processor 25 or the clinician may determine therapy programs to increase the overall lesion volume, while reducing the number of sites of therapy delivery, for example, along a vessel.

Figure 5:
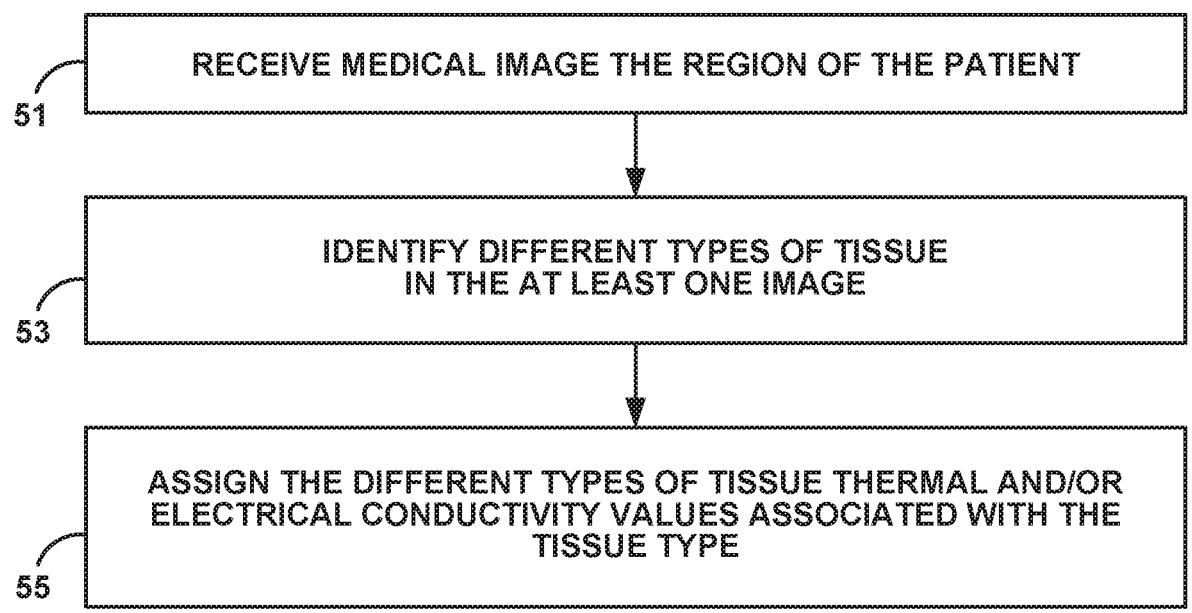
FIG. 5 is a flow diagram illustrating an example technique for generating a computer model of a region of the patient.

As discussed above, in some examples, processor 25 generates a computer model of a region of a patient, where the computer model defines a spatial representation of tissue, including respective tissue characteristics (e.g., thermal conductivity, electrical conductivity, density, and/or the like), in the region. Processor 25 may generate the computer model using any suitable technique. FIG. 5 is a flow diagram illustrating an example technique for generating a computer model of a region of the patient.

In the example of FIG. 5, processor 25 receives at least one medical image of the region the patient from medical imaging system 46 (51). Any suitable imaging modality may be used for the medical image, examples of which are described above. Based on the at least one image, processor 25 may identify different types of tissue in the at least one image (53). Example tissue types include, but are not limited to, bones, tendons, muscle, fat, lymph nodes, blood vessels, and/or organs. As another example, example tissue types may merely be based on the tissue characteristics, such as, but not limited to, the thermal or electrical conductivity of the tissue, the density of the tissue, the chemical diffusivity of the tissue, sonic or ultrasonic parameters, for example, speed of sound or attenuation, or the like or any combination thereof.

For example, processor 25 may identify predetermined tissue types in the at least one image based on location, size, or one or more visual characteristics of the image (e.g., depth of the color of the image), or coordinating with expected densities of different tissue types. As another example, processor 25 may receive user input via user interface 26 (FIG. 3) that identifies different tissue types in the image. For example, a user may provide input outlining different sub-regions of tissue types and identifies the tissue types, such as by assigning the different sub-regions a particular tissue type. Processor 25, however, may also do this automatically in some examples, such as by using image processing techniques, e.g., edge detection, to find boundaries between different tissue types. By identifying the different types of tissue in the at least one image, processor 25 may generate a map of the region of the patient, which indicates the relative location and types of tissue proximate a target nerve and associated blood vessel.

Processor 25 may assign the different types of tissue corresponding tissue characteristics associated with known tissue types (55). For example, processor 25 may assign different identified tissue types within the medical image respective thermal and/or electrical conductivity values, optical transmittivity, or chemical diffusivity values associated with the respective tissue types. In some examples, one or more of thermal or electrical conductivities and tissue densities for different tissue types may be generic to patients, or at least to some classes of patients (e.g., tissue characteristics of newborns may be similar to each other, while tissue characteristics of geriatric patients may be similar to each other). Processor 25 may associate different tissue types with respective tissue characteristics in memory 28 (FIG. 3) of programmer 24 or a memory of another device.

Processor 25 may use, in addition to, or instead of, the at least one image, electrical maps of the patient region, for example, an impedance map determined by a plurality of electrodes introduced into the region of the patient to generate the computer model. In some examples, the clinician may designate the tissue type, and processor 25 may assign the tissue type identified by the clinician with respective tissue characteristics (for example, thermal and electrical conductivities and density). In this way, by combining tissue characteristics with spatial relationships of different tissue types identified in the at least one image, processor 25 may generate computer model 32 representing tissue characteristics at different sites within the patient region in the image. The computer model 32 may be, for example, a digital reconstruction of the region of the patient.

In some examples, processor 25 may process multiple images to generate a 2D or 3D computer model 32. The electrical maps and/or images may be registered to each other using any suitable, such as by aligning anatomical landmarks (e.g., boney landmarks) visible in the images and/or maps.

Figure 6:
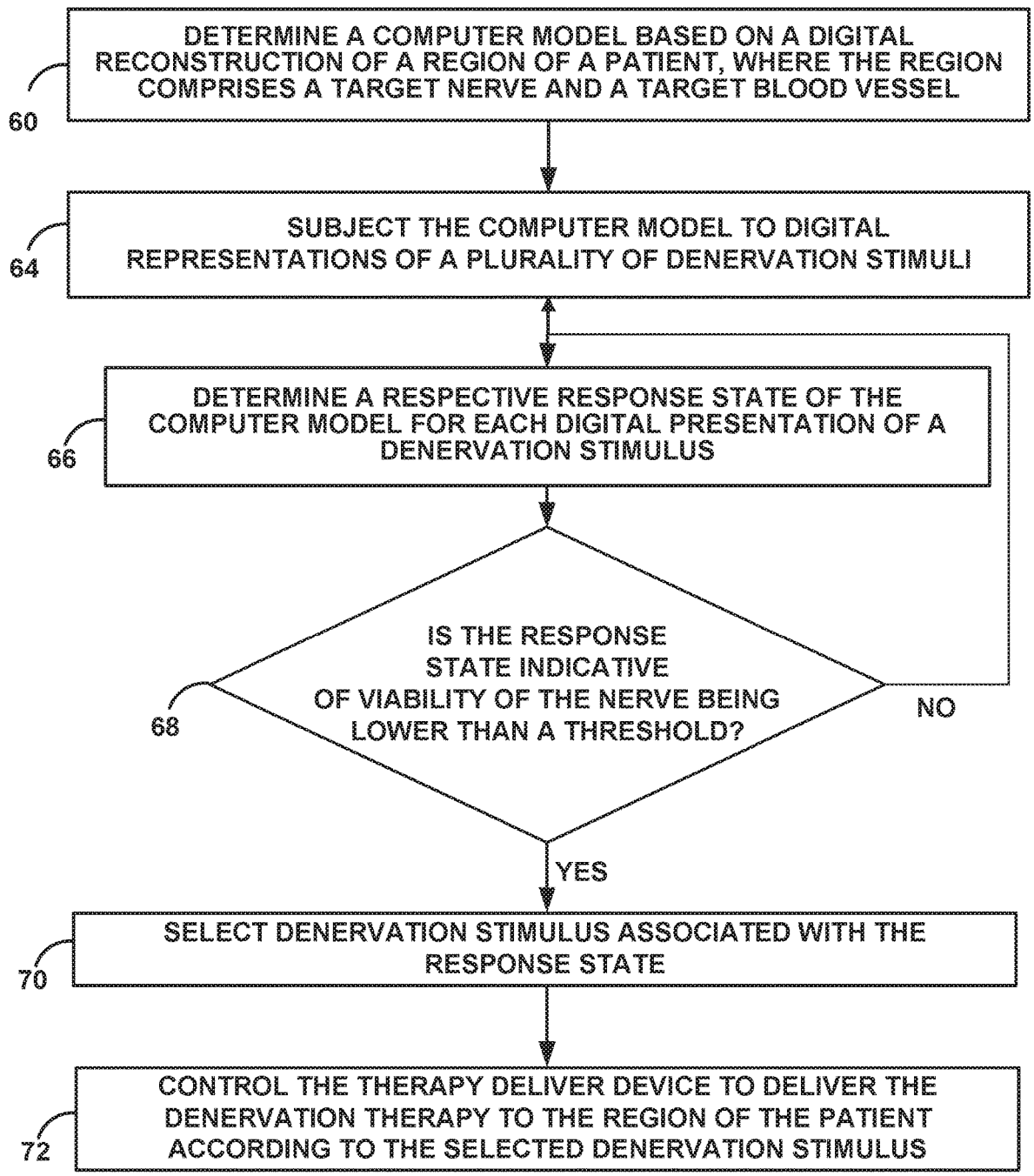
FIG. 6 is a flow diagram illustrating an example technique for delivering denervation therapy.

FIG. 6 is a flow diagram illustrating another example technique for delivering denervation therapy. The technique shown in FIG. 6 may be a more specific example of the technique of FIG. 4. In some examples of the technique shown in FIG. 6, processor 25 determines a computer model 32 based on a digital reconstruction 30 of a region of a patient (60). The region includes a target nerve and a blood vessel. Computer model 32 defines a spatial representation of one or more tissue characteristics in the region. Processor 25 can determine computer model 32 by generating computer model 32, e.g., using the technique described with respect to FIG. 5, or by retrieving an already-generated computer model 32 from memory 28 of programmer 24 or a memory of another device.

Processor 25 subjects computer model 32 to digital representations of a plurality of denervation stimuli (64). For each of the digital representations of a denervation stimulus, processor 25 simulates the delivery of the respective denervation stimulus the digital reconstruction of tissue of the patient by (a digital representation of) therapy delivery device 12 in a respective pre-determined orientation and at a respective predetermined location along the blood vessel. Processor 25 determines a respective response state of computer model 32 to each of the digital representations of a denervation stimulus (66). For example, processor 25 may generate the estimated volume of influence based on the magnitude, orientation, and direction of the denervation stimulus, and based on the tissue properties (as represented in computer model 32) of tissue adjacent the target nerve and the blood vessel. The response state may indicate how far the denervating effects of the denervation stimulus are expected to propagate from the therapy delivery device 12 within the patient, given the tissue characteristics of tissue proximate the therapy delivery elements of therapy delivery device 12.

In the technique shown in FIG. 6, processor 25 generates an estimated volume of influence expected to result from delivery of denervation therapy delivery device 12 according to a particular therapy program by subjecting computer model 32 to the digital representations of the plurality of denervation stimuli and determining the response state of the computer model 32 to the respective denervation stimulus.

Processor 25 may select the denervation stimulus for therapy delivery to the patient based on the determined response states. For example, processor 25 may determine a viability of the target nerve based on the response state, and may compare the viability with a threshold (68). In some examples, processor 25 may determine viability based on temperature the target nerve or adjacent tissue is expected to attain, and the time period for which the target nerve or adjacent tissue is expected to maintain the temperature. For example, a lower time duration may be sufficient to affect viability if the expected temperature is relatively higher. If the viability of the nerve is less than the threshold, then the response state may be indicative of denervation of the target nerve (because the viability of the nerve reduced to below the threshold). In some such examples, processor 25 may select the at least one denervation stimulus in response to determining that the respective response state associated with the selected at least one denervation stimulus is indicative of viability of the nerve being lower than a threshold (70). In such examples, processor 25 may store the therapy program used to generate the denervation stimulus in therapy programs 34 as an efficacious therapy program, or by storing the therapy program as a new therapy program added to therapy programs 34. In some examples, processor 25 may associate that therapy program with the particular target nerve, so that processor 25 or another device may select the therapy program if that target nerve is to be denervated. In some examples, the target nerve may be a member of a nerve bundle, the therapy program may be associated with the nerve bundle.

In some examples, the region of the patient includes at least one non-target non-nerve tissue. In some such examples, in addition to or instead of non-viability or low viability of the target nerve, a sufficiently high viability of a non-target tissue (for example, non-nerve tissue or organ) may be sought. In some such examples, the respective response state associated with the selected at least one denervation stimulus may be indicative of viability of the non-target non-nerve tissue being greater than the threshold. Thus, in some examples, processor 25 selects the at least one denervation stimulus in response to determining that the respective response state associated with the selected at least one denervation stimulus is indicative of viability of the non-target non-nerve tissue being greater than a threshold. Processor 25 may store the therapy program used to generate the denervation stimulus in therapy programs 34 as an efficacious therapy program, or by storing the therapy program as a new therapy program added to therapy programs 34. In some examples, processor 25 may associate that therapy program with the particular target nerve, so that processor 25 or another device may select the therapy program if that target nerve is to be denervated.

Processor 25 may subsequently use the one or more selected denervation stimuli (or resulting therapy programs) to control delivery denervation therapy by generator 14. For example, processor 25 may control generator 14 to generate and deliver the denervation therapy to the region of the patient via therapy delivery element 12 according to the denervation stimuli (or resulting therapy programs) (72).

While a clinician may deploy and manipulate the position, orientation, and initiation of denervation stimulus delivery via therapy delivery device 12, in some examples, programmer 24 may control or help the clinician with automated or semi-automated positioning, orienting, or triggering of therapy delivery device.

Figure 7:
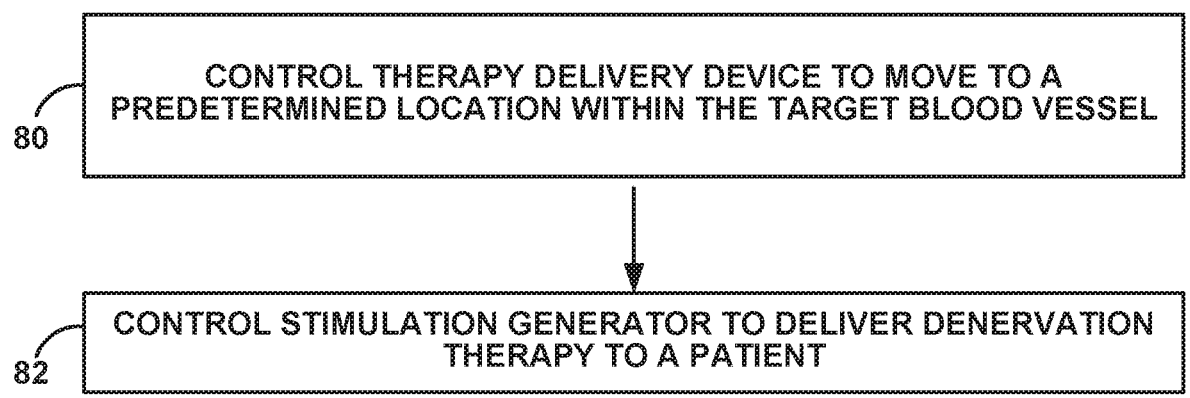
FIG. 7 is a flow diagram illustrating an example technique for delivering denervation therapy.

FIG. 7 is a flow diagram illustrating an example technique for controlling the position of therapy delivery device 12 within patient during a medical procedure. Memory 28 of programmer 24 or a memory of another device may store a plurality of indexed locations for therapy delivery device 12. The indexed locations may correspond to locations (e.g., relative to some known landmark) at which a therapy delivery element of device 12 may be positioned along a length of a blood vessel to provide an even distribution of denervation stimuli. In addition, or instead, the indexed locations may correspond to particular therapy programs selected for the respective location to provide the desirable volumes of influence. As discussed above, because of varying tissue characteristics at different positions along a blood vessel, the denervation therapy parameter values needed to generate a volume of influence that results in the desired therapeutic effect may differ based on the location within the patient. The technique of FIG. 7 may help system 10 provide more efficient and effective denervation therapy in a shorter amount of time by associating known locations with respect therapy programs that have been determined (using computer model 32) to likely result in efficacious therapy delivery to the patient.

In accordance with the technique shown in FIG. 7, processor 25 controls a surgical device to move therapy delivery device 12 to a predetermined location within the blood vessel (80). For example, processor 25 may send one or more control signals through drive circuitry 41 or otherwise to drive unit 48, and drive unit 48 may engage therapy delivery device 12, and cause therapy delivery device 12 to advance, retract, or rotate to assume a predetermined position and orientation along the blood vessel and relative to the target nerve or predetermined non-nerve tissue. Once therapy delivery device 12 is at the desired, predetermined location, processor 25 may control generator 14 to deliver denervation therapy to a patient based on the one or more therapy parameter values (82). For example, processor 25 may send generator 14 a control signal that causes generator 14 to deliver the denervation stimulus. As another example, processor 25 may notify a clinician, who may then manually control generator 14 to deliver the denervation stimulus.

As discussed above, in some examples, processor 25 generates a GUI 26 and presents the GUI on a display of user interface 26 of programmer 24. The GUI may present, for example, a graphical representation of a region of a patient that includes a target nerve and, if relevant, a corresponding blood vessel. The corresponding blood vessel can be, for example, a blood vessel through which therapy delivery device 12 is introduced to access the target nerve. In some examples, the GUI may only include a graphical representation of a region of a patient that includes a target nerve and, if relevant, a corresponding blood vessel. In other examples, the GUI may include other graphical elements, such as a graphical representation of an estimated volume of influence expected to result from delivery of a denervation stimulus to tissue of the patient via therapy delivery element 12. In some examples, the GUI or another display (for example, a fluoroscopic display) may include a graphical representation of one or more of a series of target locations for delivering therapy determined by processor 25, and may include not include a graphical representation of the estimated volume of influence. Such a GUI may help a clinician better visualize the denervation therapy and gain a better understanding of the affects that different therapy parameter values, including the location of a therapy delivery element within the patient, may have on the volume of influence.

In some examples, rather than generating a graphical representation of a volume of influence based on a known therapy program as discussed in some examples above, a user may provide input indicating a graphical representation of a desired volume of influence within the GUI, and processor 25, in response, may determine the therapy parameter values that are expected to result in the volume of influence. Processor 25 may then program generator 14 using these therapy parameter values, which may be stored as a therapy program.

Figure 8:
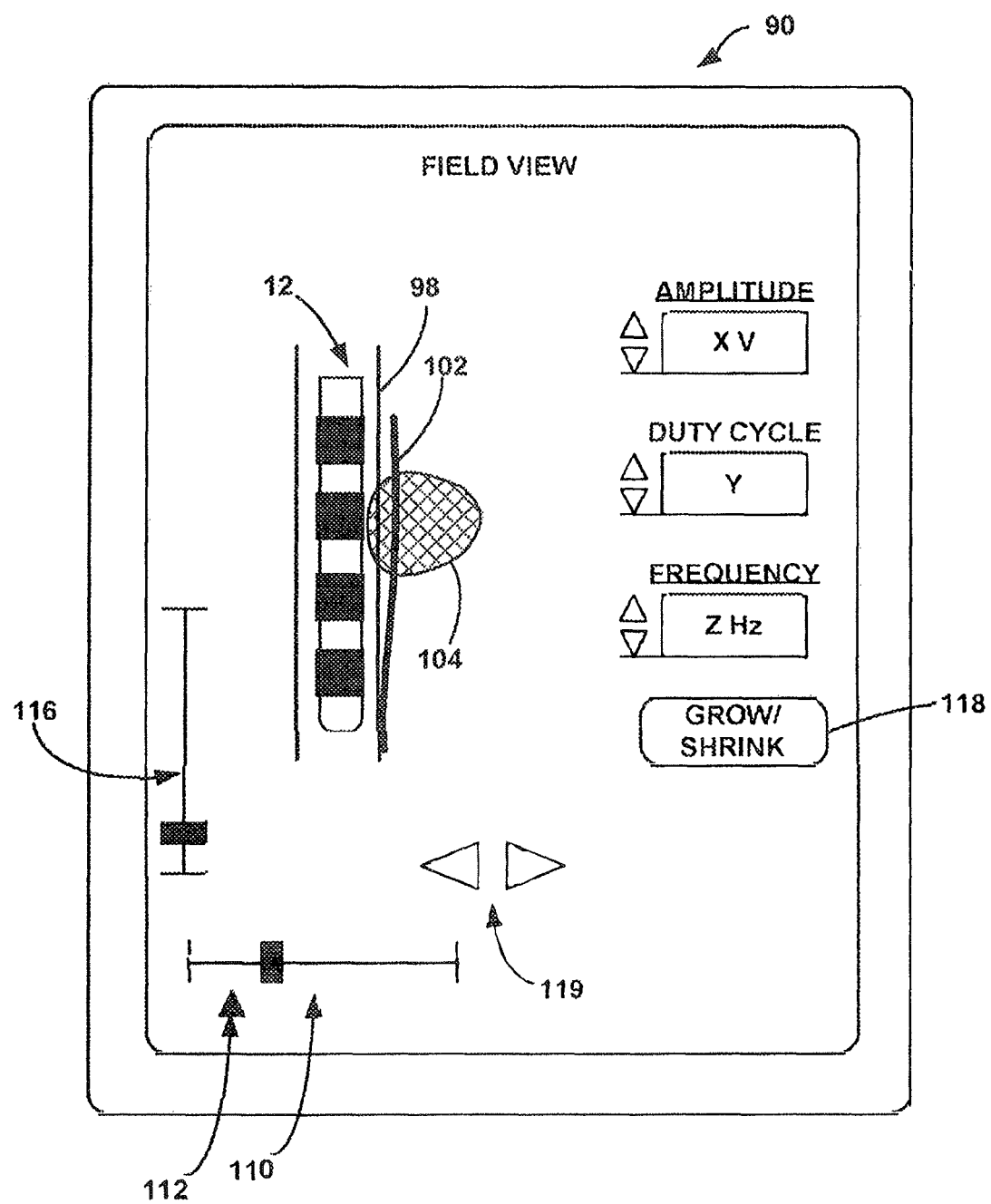
FIG. 8 illustrates a schematic representation of an example graphical user interface (GUI) that may be presented on a display of a user interface of the programmer of FIG. 3.

FIG. 8 illustrates a schematic representation of an example GUI 90 that may be presented on the display of user interface 26 of programmer 24 of FIG. 3. By interacting with GUI 90, a user may generate a graphical representation of an electrical stimulation field, which may be an example of a volume of influence. In some examples, the user may be able to create a stimulation field and direct processor 25 to generate a set of therapy parameter values (e.g., a therapy program) that would best match the stimulation field. In some examples, the user may change the size, shape or position of the stimulation field within GUI 90 using graphical input media such as cursor or stylus control. The generated electrical stimulation field may be utilized as a computer model of a therapy field associated with the generated parameters, for example, the volume of influence associated with electrical denervation stimuli. Thus, the volume of influence may be observed by the clinician using GUI 90, and the clinician may select or modify one or more of therapy programs 34 based on the observed volume of influence.

GUI 90 illustrates a graphical representation of therapy delivery device 12, which includes a multi-electrode geometry. In the example of FIG. 8, therapy delivery device 12 includes four electrodes at different axial positions, generally arranged in a ring. Each electrode is coupled to a respective electrical conductor within therapy delivery device 12. Hence, therapy delivery device 12 includes multiple electrical conductors, e.g., wires, cables or the like, that extend from the proximal end of the lead to respective electrodes to electrically couple the electrodes to electrical terminals, for example, those of generator 14.

Each electrode is powered independently by generator 14 so that stimulation energy can be delivered at different axial and angular positions. In some examples, therapy delivery device 12 may include combinations of complex electrode array geometries and simple electrode array geometries. For example, ring electrodes that extend about the entire circumference of the lead may be used in combination with electrodes disposed at different axial and angular positions. Selective activation of the electrodes carried by therapy delivery device 12 can produce customizable stimulation fields that may be directed to a particular side of therapy delivery device 12 in order to isolate the stimulation field around a target anatomical region.

GUI 90 illustrates a side view of therapy delivery device 12, shown to be introduced in a blood vessel 98. Although not shown in FIG. 8 or 9, the graphical representation of therapy delivery device 12 may be spiral and in contact with the inner walls of the graphical representation of blood vessel 98. The size and shape of a stimulation field 104 generated by therapy delivery device 12 may be established based on the generic physical characteristics of tissue, as well as based on known physical characteristics of the electrodes of therapy delivery device 12. In other words, stimulation field 104 displayed in GUI 90 may only be an approximation of what the stimulation field would be in the region of the patient including the target nerve. However, in some examples, physical characteristics of the actual anatomical structure of the patient being treated may be used to generate stimulation field 104. This anatomical structure information may be presented to programmer 24 in the form of patient anatomical data generated by an imaging modality, such as CT, MRI, or any other volumetric imaging system and stored within memory 28 (FIG. 3). Processor 25 may generate stimulation field 104 using, for example, tissue impedance models, field propagation models, or the like. In some examples, stimulation field 104 may be a representation of an electrical field, current density, voltage gradient, or neuron activation, applied to a generic human tissue or patient-specific tissue characteristics. In addition, the user may be able to switch between any of these representations when desired.

The user may move stimulation field 104 up or down relative to a longitudinal axis of therapy delivery device 12 using vertical scroll bar 116 or some similar control interface. As stimulation field 104 moves up or down in response to the user input, programmer 24 automatically selects appropriate electrode(s) to support the vertical movement of stimulation field 104 within GUI 90. GUI 90 includes arrows 119 or similar input media that permit the user to transition between different rotational views.

In addition, the user may rotate the view shown in GUI 90 using horizontal scroll bar 110 or some similar control device, e.g., to visualize stimulation field 104 relative to other tissue sites not shown in all views. An arrow 112 may be provided next to horizontal scroll bar 110 to indicate the orientation of therapy delivery device 12 relative to an anatomical structure.

Movement of stimulation field 104 within GUI 90 using scroll bars 116 or similar input media may permit the user to evaluate different stimulation field positions without the need to manually select electrodes and manually enter parameter values. Instead, processor 25 of programmer 24 automatically selects electrodes and parameter values in response to movement of stimulation field 104 by the user. Although scroll bar 116 is illustrated as examples of input media for movement of stimulation field 104, other types of input media may be used. Examples include up/down arrows or side-to-side arrows, which may be presented on a touch screen or formed by buttons or keys on programmer 24.

As a further alternative to manipulating the stimulation field 104, the user may select stimulation field 104 with a stylus, mouse, or other pointing device and drag the field upward, downward, or rotationally. In some examples, a mouse or other pointing device may support left or right click functionality to perform different operations relative to stimulation field 104. With a stylus, a first click on stimulation field 104 may initiate movement, dragging with the stylus directs movement relative to the schematic illustration of therapy delivery device 12 in GUI 90, and a second click may terminate movement. In each case, processor 25 of programmer 24 responds to the specified movement by automatically adjusting the electrode combination and the stimulation parameters to approximate the characteristics of stimulation field 104 presented by GUI 90. As the stimulation parameter values change, the size and shape of stimulation field 104 presented on the display change. Similarly, as the electrode combination changes in terms of polarity or electrode selection, the size, shape or direction of stimulation field 104 presented on the display changes.

In some examples, processor 25 of programmer 24 may utilize stimulation templates and select the best fitting stimulation template set to a newly modified stimulation field 104 in order to generate therapy parameter values for achieving stimulation field 104. A stimulation template is a predetermined volumetric stimulation field that processor 25 of programmer 24 may substantially match to a desired stimulation field 104 from the user. An algorithm for generating stimulation parameter values that fit the user defined stimulation field may be less computationally intensive for processor 25 compared to an algorithm that references multiple equations or lookup tables to generate the stimulation parameters. The stimulation template may be a representation of an electrical field or other electrical stimulation related characteristic, e.g., current density, voltage gradient, or neuron activation, applied to a generic human tissue. For stored stimulation templates, processor 25 may adjust the RF energy to alter the size of the stimulation template to cover the desired stimulation field 104 from the user.

Processor 25 of programmer 24 may limit the rate of movement of stimulation field 104 within GUI 90. In other words, stimulation field 104 may only be moved a certain number of steps per second within GUI 90, or any other user interface that allows the user to drag the stimulation field. This rate movement limit may prevent unnecessary calculations or ensure patient comfort in real-time programming examples.

In addition to moving stimulation field 104, GUI 90 may permit the user to perform one or more operations that result in reconfiguration of stimulation field 104. For example, the user may click on a border, i.e., an outer perimeter, of stimulation field 104, and drag it inward or outward to resize the stimulation field. Resizing by enlarging or shrinking stimulation field 104 in GUI 90 may result in an increase or decrease in RF energy, and, therefore, changes to the parameter values of a therapy program used to generate stimulation field 104. In some examples, enlarging or shrinking stimulation field 104 also may result in selection or de-selection of electrodes included in the existing electrode combination. In either case, processor 25 of programmer 24 adjusts the electrode combination and/or parameter values in response to the enlargement or shrinkage of stimulation field 104 by the user.

When a user clicks on stimulation field 104 border and drags it, the entire stimulation field may be expanded in two dimensions in equal proportions. Alternatively, stimulation field 104 may expand only in the direction in which the user drags the stimulation field. For example, horizontal dragging of the field perimeter to enlarge stimulation field 104 may result in overall enlargement of the cross-sectional seize of stimulation field 104, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, programmer 24 may provide different aspect ratio modes on a selective basis for expansion and shrinkage of stimulation field 104.

To enlarge or shrink stimulation field 104, the user may simply click on the stimulation field border within GUI 90. Alternatively, the user may click on a grow/shrink button 118 as shown in FIG. 8, and then click on the border of stimulation field 104 to drag it inward or outward and thereby adjust the size of the stimulation field. In response, processor 25 of programmer 24 may automatically reconfigure the selected electrode(s) and/or stimulation parameter values to approximate the resized stimulation field. In this way, a user may generate a volume of influence by directly manipulating the stimulation field 104. In each case, the user changes stimulation field 104 by simply changing the representation of the stimulation field 104 presented on GUI 90, thereby avoiding the need to manually select electrodes and parameter values.

A user may manipulate the size, shape, and/or location of stimulation field 104 (or another type of volume of influence in other examples) in order to, for example, better target a target nerve and/or to avoid an adverse-effect region. Thus, although not shown in FIG. 8, GUI 90 may include a graphical representation of the target nerve, an adverse-effect region, and/or other tissue sites of interest, or may at least include a medical image of the region of the patient overlaid with the graphical representation of therapy delivery element 12 and stimulation field 104. In some cases, a target nerve may not be visible in a medical image. In these examples, a graphical representation of an adverse-effect region, and/or other tissue sites of interest may still be useful information to present, as it would still guide a user to select denervation therapy parameter values that may avoid the adverse-effect region.

After selecting a desirable stimulation field 104, processor 25 of programmer 24 may determine the one or more therapy parameter values that are expected to result in the desirable stimulation field 104, e.g., based on computer model 32. Processor 25 may, in some examples, control generator 14 or another medical device to deliver denervation therapy to the region of the patient in accordance with the one or more therapy parameter values.

Figure 9:
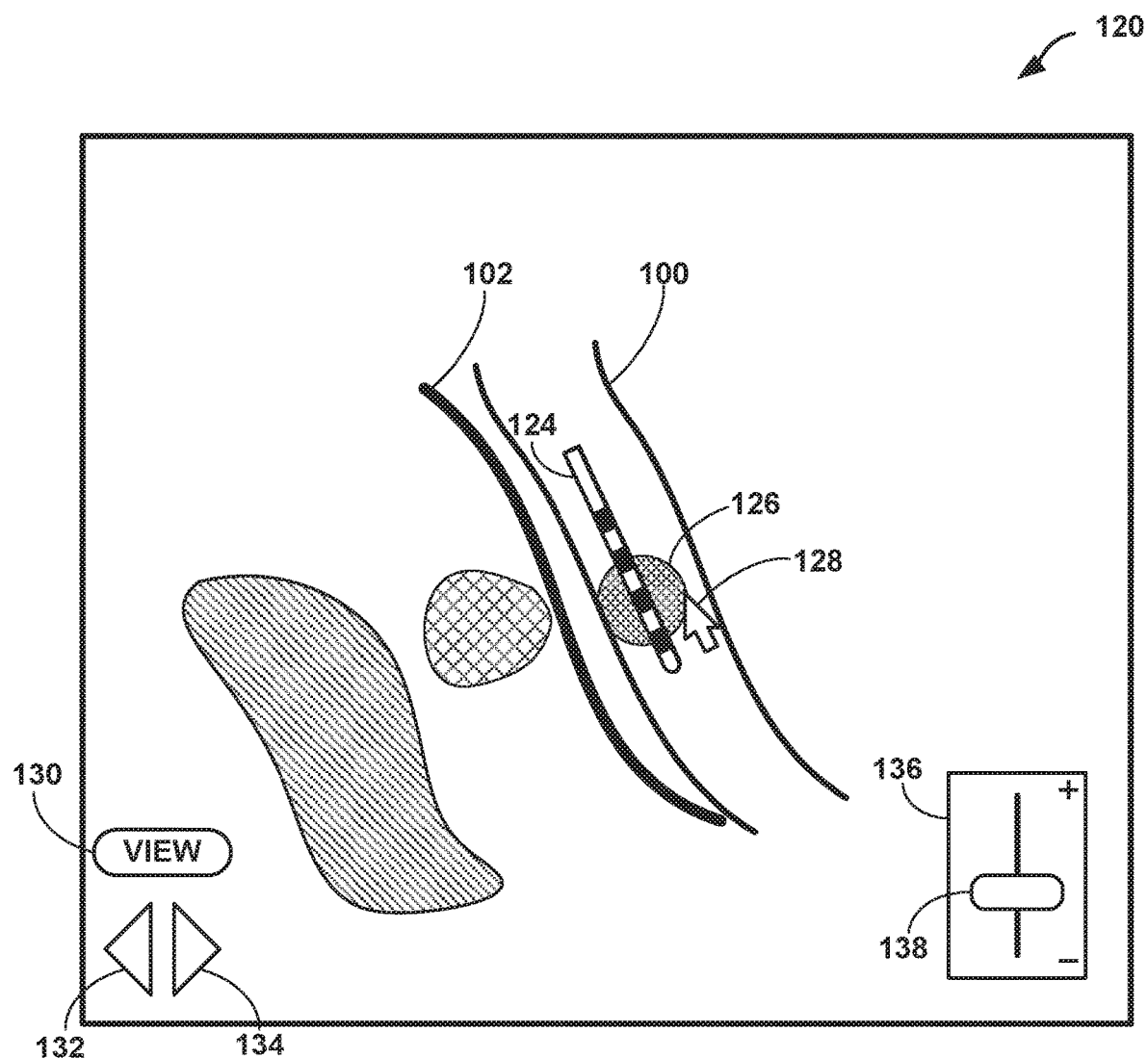
FIG. 9 is a schematic illustration of another example of a GUI that may be presented on the display of the programmer of FIG. 3.

FIG. 9 is a schematic illustration of another example of a GUI 120 that may be presented on the display of programmer 24. A user may interact with GUI 120 via user interface 26 of programmer 24 in order to select a desired volume of influence of denervation therapy. GUI 120 includes a representation of an anatomical region of a patient, for example, a region including target nerve 102. In GUI 120, a device icon 124 representing therapy delivery device 12 is displayed within a graphical representation of blood vessel 100.

Differently shaded portions of GUI 120 indicate varying densities of tissue within the region. For example, darker portions may indicate more dense tissue. A user may be able to recognize different anatomical structures or tissue types by viewing GUI 120. It should be noted that display 120 shown in FIG. 9 is merely an example image, and actual images may include a wider range of shades and higher image resolution.

Display 120 further includes pointer 128, previous arrow 132, next arrow 134, fine control input mechanism 136, and control slide 138. Pointer 128 may be controlled with a mouse and buttons, a track-ball, touch-pad, touch screen or other movement input device, which may be a part of user interface 26 of programmer 24. A user may use pointer 128 to drag device icon 124 into position or rotate device icon 124. The user may zoom in to or out of the view for a larger view of anatomical region, or move up, down, left, or right to view a larger or smaller portion of the region.

GUI 120 allows the user to select and adjust a size, and, in some examples, a shape of volume of influence 126, which may be further defined in other orthogonal views. The user may use pointer 128 to drag volume of influence 126 to define a smaller or larger size, which may correspond to a lower or higher RF energy level. For example, the user may click on a border, or perimeter of volume of influence 126, and then drag the border to expand or contract volume of influence 126. This adjustment is the coarse control of the size of volume of influence 126. The user may use pointer 128 to move control slide 138 up to slightly increase the size of volume of influence 126 or down to slightly decrease the size of volume of influence 126.

Processor 25 of programmer 24 may limit the rate of movement of volume of influence 126. For example, processor 25 may limit the movement of volume of influence 126 within GUI 120 to a certain number of steps per second. This rate movement limit may prevent unnecessary calculations in real-time changing of denervation therapy parameter values parameters with modifications of volume of influence 126.

View button 130 may permit a user to switch to another view of the region. The other views may include, for example, a view from a different orientation, or a view based on a different imaging technique.

The following discussion provides further details regarding patient anatomy and physiology as it may relate to renal denervation therapy. This section is intended to supplement and expand upon the previous discussion regarding the relevant anatomy and physiology, and to provide additional context regarding the disclosed technology and the therapeutic benefits associated with renal denervation. For example, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of a therapy delivery device and a luminal surface or wall of the renal artery, and/or effectively modulating the renal nerves with the therapy delivery device.

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla. Once released, norepinephrine and epinephrine bind adrenergic receptors on peripheral tissues. Binding to adrenergic receptors may cause a neuronal and hormonal response. The physiologic manifestations include one or more of pupil dilation, increased heart rate, occasional vomiting, or increased blood pressure. Increased sweating can also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Figure 10:
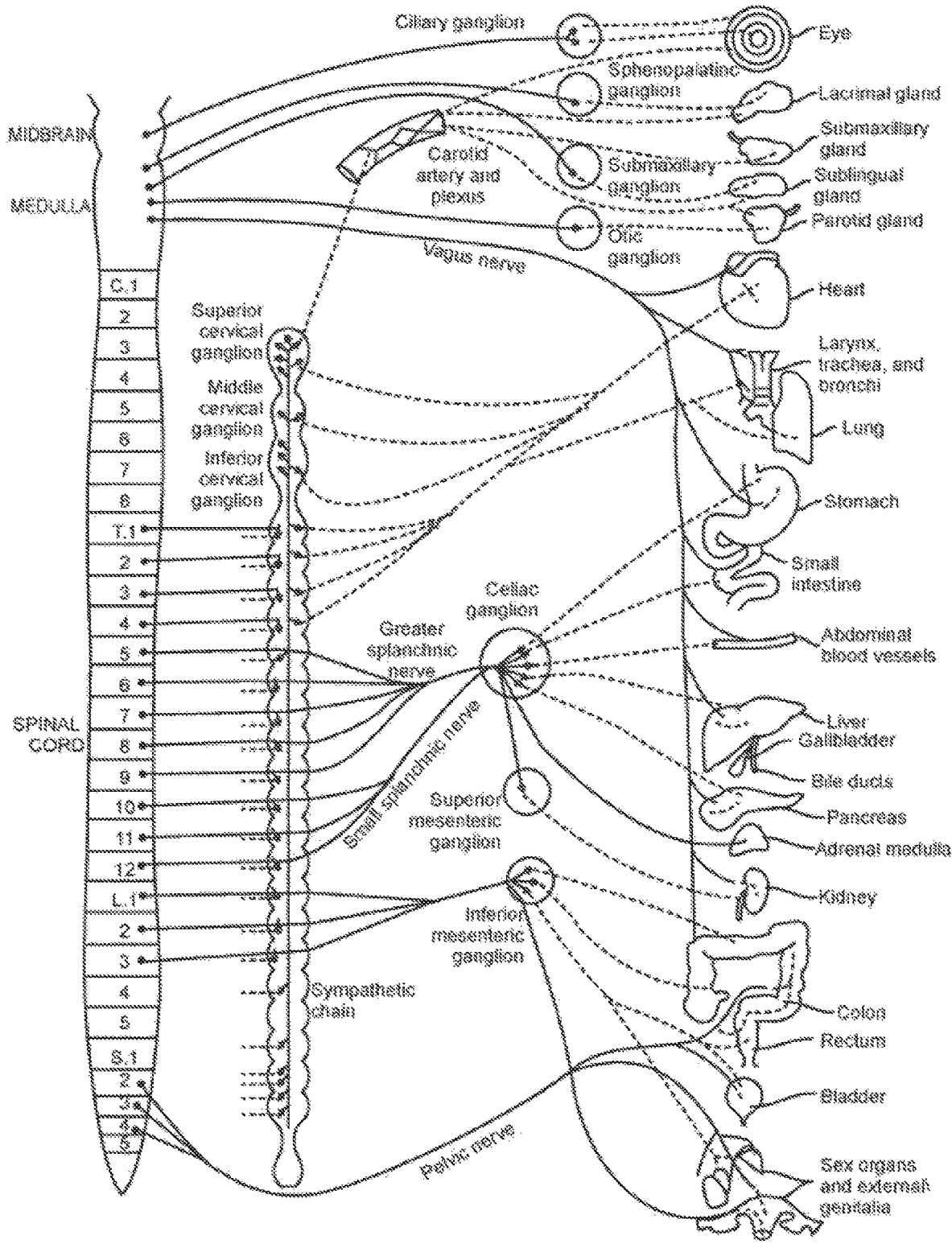
FIG. 10 is a conceptual and schematic illustration of the sympathetic nervous system (SNS) and communication between the brain and the body via the SNS.

FIG. 10 is a conceptual and schematic illustration of the sympathetic nervous system (SNS) of a human subject. As shown in FIG. 10, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

Figure 11:
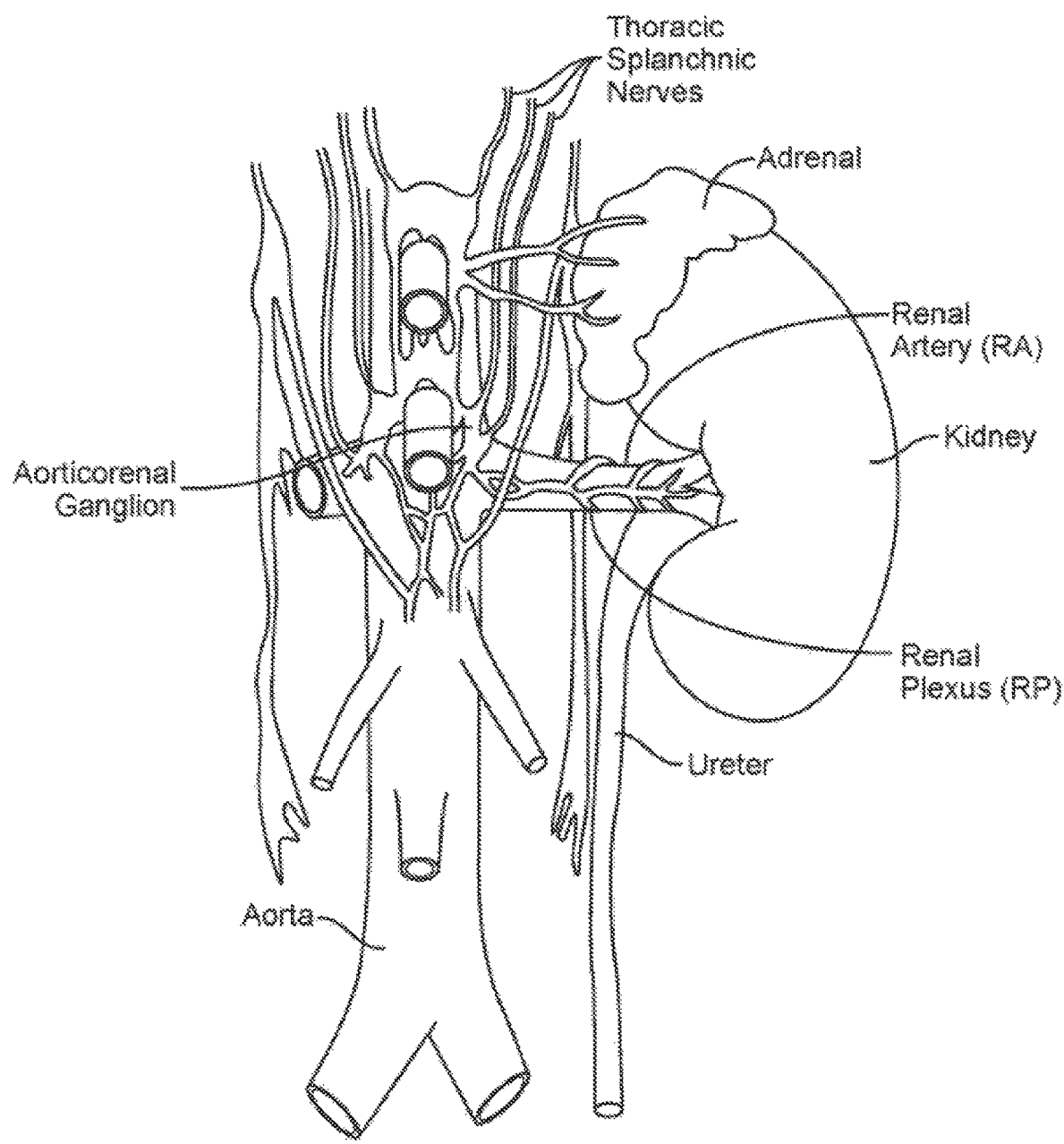
FIG. 11 is a conceptual anatomic view of nerves innervating a left kidney to form the renal plexus surrounding the left renal artery.

FIG. 11 is a conceptual anatomic view of nerves innervating a left kidney to form the renal plexus surrounding the left renal artery of a human subject. As shown in FIG. 11, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that can result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity can be even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). However, the current pharmacologic strategies have significant limitations including limited efficacy, compliance issues, side effects and others.

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication.

Figure 12A:
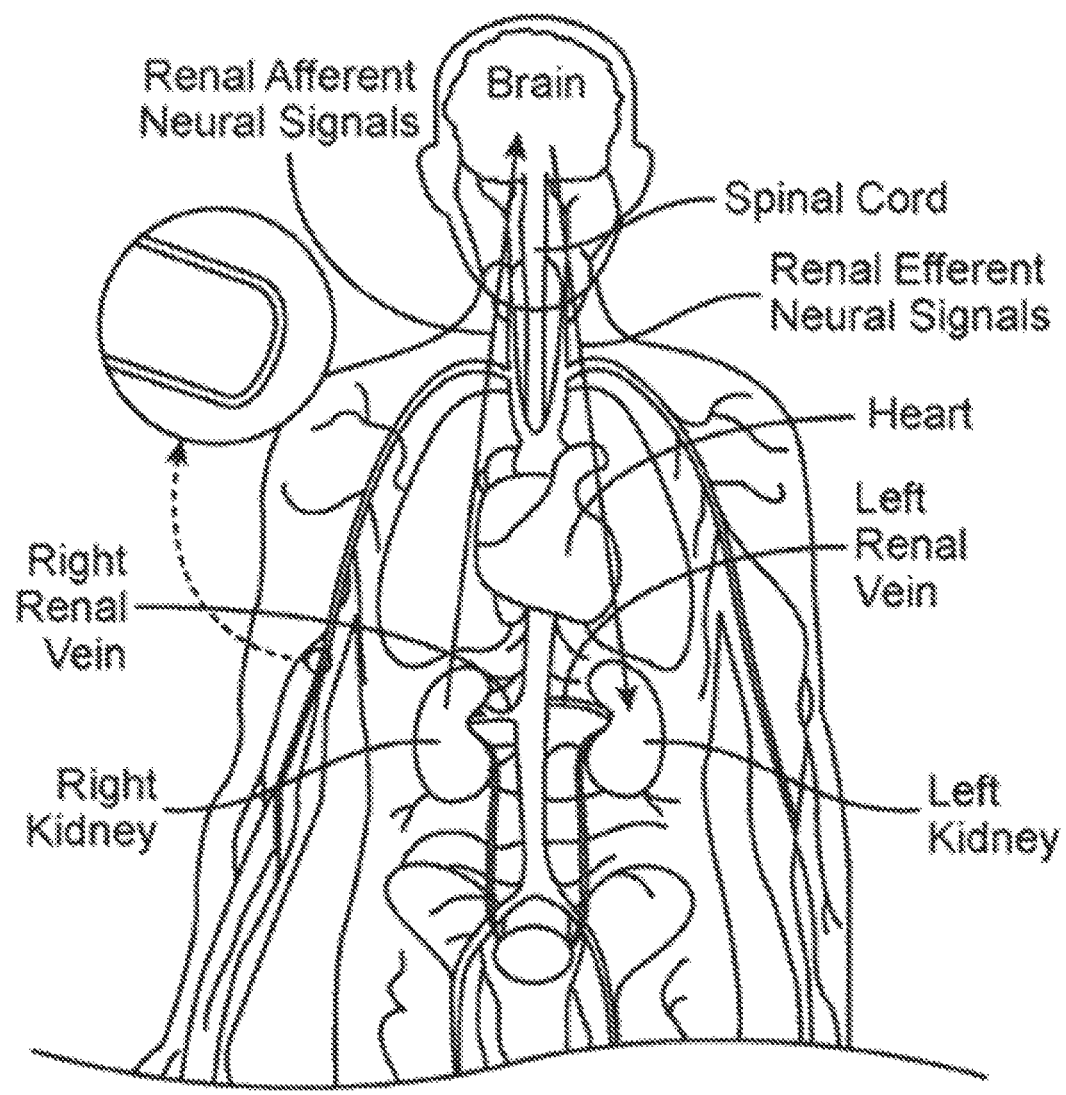
FIGS. 12A and 12B are conceptual anatomic views of a human body, respectively, depicting neural efferent and afferent communication between the brain and kidneys.
Figure 12B:
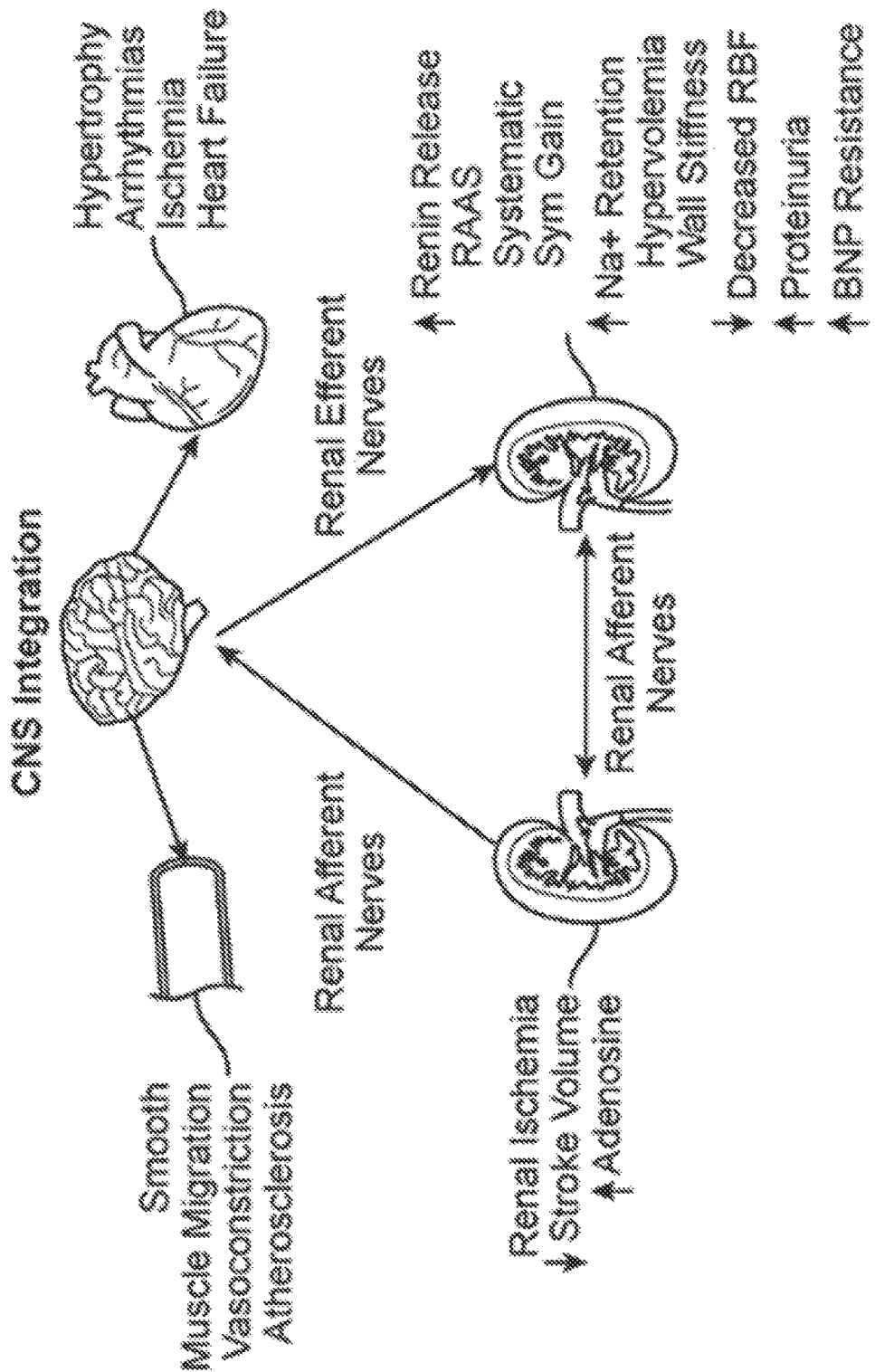

FIGS. 12A and 12B are conceptual anatomic views of a human body, respectively, depicting neural efferent and afferent communication between the brain and kidneys. As shown in FIGS. 12A and 12B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore indicates that (i) modulation of tissue with efferent sympathetic nerves may reduce inappropriate renin release, salt retention, and reduction of renal blood flow, and that (ii) modulation of tissue with afferent sensory nerves may reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

As provided above, renal denervation may be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Because the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 10. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

In accordance with the present technology, neuromodulation (e.g., denervation) of a left and/or right renal plexus RP, which is intimately associated with a left and/or right renal artery, may be achieved through intravascular access.

FIGS. 13A and 13B are, respectively, conceptual anatomic views of the arterial and venous vasculatures of a human subject. As shown in FIG. 13A, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As shown in FIG. 13B, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

The femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region may provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

Because neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter or another therapy delivery device may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatuses, systems, and methods for achieving renal neuromodulation via intravascular access may account for these and other aspects of renal arterial anatomy and its variation across the patient population when minimally invasively accessing a renal artery.

In addition to complicating renal arterial access, specifics of the renal anatomy may also complicate establishment of stable contact between a therapy delivery device and a luminal surface or wall of a renal artery. When the therapy delivery device includes an energy delivery element, such as an electrode, consistent positioning and appropriate contact force applied by the energy delivery element to the vessel wall may be desirable for predictable denervation therapy delivery. However, navigation may be impeded by the tight space within a renal artery, as well as tortuosity of the artery. Furthermore, establishing consistent contact may be complicated by patient movement, respiration, and/or the cardiac cycle because these factors may cause significant movement of the renal artery relative to the aorta, and the cardiac cycle may transiently distend the renal artery (i.e., cause the wall of the artery to pulse.

Even after accessing a renal artery and facilitating stable contact between therapy delivery device and a luminal surface of the artery, nerves in and around the adventitia of the artery may be safely modulated via the therapy delivery device. Effectively applying thermal treatment from within a renal artery can be non-trivial given the potential clinical complications associated with such treatment. For example, the intima and media of the renal artery are relatively vulnerable to thermal injury. As discussed in greater detail below, the intima-media thickness separating the vessel lumen from its adventitia means that target renal nerves may be multiple millimeters distant from the luminal surface of the artery. Sufficient energy may be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery may be applied carefully. Accordingly, the complex fluid mechanics and thermodynamic conditions present in the renal artery during treatment, particularly those that may impact heat transfer dynamics at the treatment site, may be accounted for in applying energy (e.g., heating thermal energy) and/or removing heat from the tissue (e.g., cooling thermal conditions) from within the renal artery.

The therapy delivery device may also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the therapy delivery device to multiple treatment locations may be desirable, and may be aided by the computer modeling techniques described above. It should be noted, however, that a benefit of creating a circumferential ablation may outweigh the potential of renal artery stenosis or may be mitigated with certain embodiments or in certain patients and creating a circumferential ablation could be a goal. Additionally, variable positioning and repositioning of the therapy delivery device may prove to be useful in circumstances where the renal artery is particularly tortuous or where there are proximal branch vessels off the renal artery main vessel, making treatment in certain locations challenging. Manipulation of a device in a renal artery may also consider potentially adverse mechanical interaction between the device and the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time may be avoided because to prevent injury to the kidney such as ischemia. It could be beneficial to avoid occlusion all together or, if occlusion is beneficial, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery may conform to the geometry of the artery. Renal artery vessel diameter, DRA, may be in a range of about 2-10 mm, with most of the patient population having a DRA of about 4 mm to about 8 mm and an average of about 6 mm. Renal artery vessel length, LRA, between its ostium at the aorta/renal artery juncture and its distal branchings, may be in a range of about 5-70 mm, and a significant portion of the patient population is may be in a range of about 20-50 mm. Because the target renal plexus is embedded within the adventitia of the renal artery, the composite Intima-Media Thickness, IMT, (i.e., the radial outward distance from the artery's luminal surface to the adventitia containing target neural structures) also is notable and may be in a range of about 0.5-2.5 mm for some patients, with an average of about 1.5 mm. Although a certain depth of treatment may reach the target neural fibers, the treatment may not be too deep (e.g., greater than 5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4 inches (about 10 centimeters) cranially with respiratory excursion. This may impart significant motion to the renal artery connecting the aorta and the kidney, thereby requiring from the therapy delivery device a unique balance of stiffness and flexibility to maintain contact between a thermal or electrical treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

The techniques described in this disclosure may be implemented, at least in part, in hardware, software, firmware, or any combination thereof. For example, various aspects of the described techniques may be implemented within processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described instructions, units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the processing circuitry. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media, for example, non-transitory computer system-readable storage media.

Various examples have been described. These and other examples are within the scope of the following claims.

What is claimed is:

1. A method comprising:
   determining, by a processor, one or more tissue characteristics of tissue proximate a target nerve and a blood vessel of a patient;
   determining, by the processor an estimated volume of influence of denervation therapy to be delivered by a therapy delivery device disposed within the blood vessel based on the one or more tissue characteristics and characteristics of the therapy delivery device;
   rendering, by the processor on a graphical user interface, a graphical representation of the tissue proximate the target nerve and the estimated volume of influence; and
   determining, by the processor, one or more therapy parameter values for denervation therapy delivery based on the estimated volume of influence.

2. The method of claim 1, wherein the estimated volume of influence comprises a lesion.

3. The method of claim 1, wherein the estimated volume of influence of the denervation therapy comprises a first estimated volume of influence of a first denervation therapy to be delivered by the therapy delivery device according to a first therapy program, the method further comprising:
   determining, by the processor, a second estimated volume of influence of a second denervation therapy to be delivered by the therapy delivery device according to a second therapy program, the second therapy program comprising at least one therapy parameter value different from a respective therapy parameter value of the first therapy program,
wherein determining the one or more therapy parameter values for denervation therapy delivery comprises selecting one of the first therapy program or the second therapy program based on the respective first and second estimated volumes of influence.

4. The method of claim 1, wherein the estimated volume of influence comprises a lesion, and wherein determining the one or more therapy parameter values for denervation therapy delivery comprises selecting the one or more therapy parameter values determined to result in lesioning of the target nerve and avoiding lesioning of a predetermined adverse-effect region.

5. The method of claim 1, wherein the one or more therapy parameter values comprises at least one of an electrical signal parameter, a thermal signal parameter, an ultrasound signal parameter, a microwave signal parameter, an optical parameter, or a chemical dosage parameter.

6. The method of claim 1, further comprising controlling, by the processor, a medical device to deliver denervation therapy to the target nerve in accordance with the one or more therapy parameter values.

7. A system comprising:
a memory configured to store one or more tissue characteristics of tissue proximate a target nerve and a blood vessel of a patient; and
a processor coupled to the memory and configured to:
determine an estimated volume of influence of denervation therapy delivered by a therapy delivery device disposed within the blood vessel based on the one or more tissue characteristics,
generate a graphical representation of the tissue proximate the target nerve and the blood vessel and the estimated volume of influence,
determine one or more therapy parameter values for delivery of denervation therapy based on the estimated volume of influence, and
control the delivery of denervation therapy to the patient based on the one or more therapy parameter values.

8. The system of claim 7, wherein the estimated volume of influence comprises a lesion.

9. The system of claim 7, wherein the estimated volume of influence of the denervation therapy comprises a first estimated volume of influence of a first denervation therapy delivered by the therapy delivery device according to a first therapy program, the processor being further configured to:
determine a second estimated volume of influence of a second denervation therapy delivered by the therapy delivery device according to a second therapy program, the second therapy program comprising at least one therapy parameter value different from a respective therapy parameter value of the first therapy program,
wherein the processor is configured to determine the one or more therapy parameter values for the delivery of denervation therapy by selecting one of the first therapy program or the second therapy program based on the respective first and second estimated volumes of influence.

10. The system of claim 7, wherein the estimated volume of influence comprises a lesion, and wherein the processor is configured to determine the one or more therapy parameter values for the delivery of denervation therapy by selecting the one or more therapy parameter values determined to result in lesioning of the target nerve and avoiding lesioning of a predetermined adverse-effect region.

11. The system of claim 7, wherein the one or more therapy parameter values comprises at least one of an electrical signal parameter, a thermal signal parameter, an ultrasound signal parameter, a microwave signal parameter, an optical signal parameter, or a chemical dosage parameter.

12. The system of claim 7, wherein the processor is further configured to control a medical device to deliver denervation therapy to the target nerve in accordance with the one or more therapy parameter values.

13. The system of claim 7, further comprising a therapy generator configured to generate, based on the one or more therapy parameter values, a denervation stimulus.

14. The system of claim 13, further comprising the therapy delivery device configured to be coupled to the therapy generator, wherein the therapy generator is configured to deliver the denervation therapy to the patient via the therapy delivery device.

15. The system of claim 7, wherein the therapy delivery device comprises at least one of an electrode, a radiofrequency (RF) probe, a thermal probe, a cryogenic probe, a microwave probe, an ultrasonic probe, an optical source, or a chemical injector.

16. The system of claim 7, further comprising an imaging system configured to image the target nerve and the blood vessel.

17. The system of claim 16, wherein the imaging system comprises at least one of a fluoroscopy system, a computer aided tomography (CAT) scan system, a magnetic resonance imaging (MRI) system, a positron emission tomography (PET) scan system, an electrical impedance tomography (EIT) system, an ultrasound system, or an optical imaging system.

18. The system of claim 7, wherein the target nerve comprises a renal nerve and wherein the blood vessel comprises a renal artery.

19. A non-transitory computer-readable medium, comprising instructions that, when executed, cause at least one processor to:
determine one or more tissue characteristics of tissue proximate a target nerve and a blood vessel of a patient;
generate, based on the one or more tissue characteristics, an estimated volume of influence of denervation therapy delivered by a therapy delivery device disposed within the blood vessel;
generate a graphical user interface comprising a graphical representation of the tissue proximate the target nerve and the blood vessel and a graphical representation of the estimated volume of influence; and
determine one or more therapy parameter values for delivery of denervation therapy based on the estimated volume of influence.

20. A system comprising:
a therapy delivery device disposed within a blood vessel of a patient;
a processor coupled to the therapy delivery device and configured to:
determine one or more tissue characteristics of tissue proximate a target nerve and the blood vessel of the patient;
determine an estimated volume of influence of denervation therapy to be delivered by the therapy delivery device disposed within the blood vessel based on the one or more tissue characteristics and characteristics of the therapy delivery device;

render on a graphical user interface a graphical representation of the tissue proximate the target nerve and the blood vessel and the estimated volume of influence; and determine one or more therapy parameter values for denervation therapy delivery based on the estimated volume of influence.

\* \* \* \* \*